(12) United States Patent
McGee et al.

(10) Patent No.: US 10,632,309 B2
(45) Date of Patent: Apr. 28, 2020

(54) SYSTEMS AND METHODS RELATED TO THE TREATMENT OF BACK PAIN

(71) Applicant: SPR Therapeutics, LLC, Cleveland, OH (US)

(72) Inventors: Meredith McGee, Cary, NC (US); Joseph W. Boggs, II, Carrboro, NC (US); John Chae, Strongsville, OH (US); Amorn Wongsarnpigoon, Chapel Hill, NC (US); Maria E. Bennett, Beachwood, OH (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 0 days.

(21) Appl. No.: 14/952,428

(22) Filed: Nov. 25, 2015

(65) Prior Publication Data

US 2016/0213927 A1    Jul. 28, 2016

Related U.S. Application Data

(63) Continuation-in-part of application No. 13/843,002, filed on Mar. 15, 2013.

(60) Provisional application No. 61/611,560, filed on Mar. 15, 2012, provisional application No. 62/084,727, filed on Nov. 26, 2014, provisional application No. 62/091,613, filed on Dec. 14, 2014.

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/0558* (2013.01); *A61N 1/36017* (2013.01); *A61N 1/36021* (2013.01)

(58) Field of Classification Search
CPC .............. A61N 1/36071; A61N 1/0551; A61N 1/0558; A61N 1/36017; A61N 1/36021
See application file for complete search history.

(56) References Cited

U.S. PATENT DOCUMENTS

| | | | |
|---|---|---|---|
| 6,845,271 B2 | 1/2005 | Fang et al. |
| 7,337,005 B2 | 2/2008 | Kim et al. |
| 7,761,166 B2 | 7/2010 | Giftakis et al. |
| 7,792,591 B2 | 9/2010 | Rooney et al. |
| 8,249,713 B2 | 8/2012 | Fang et al. |
| 8,463,383 B2 | 6/2013 | Sakai et al. |

(Continued)

OTHER PUBLICATIONS

Patent Cooperation Treaty (PCT), International Search Report and Written Opinion for Application PCT/US2013/032627 filed Mar. 15, 2013, dated Jun. 4, 2013, 14 pgs., International Searching Authority, US.

(Continued)

*Primary Examiner* — Joseph M Dietrich
(74) *Attorney, Agent, or Firm* — McDonald Hopkins LLC

(57) ABSTRACT

The present invention reduces pain and improves function long-term in persons with back pain using electrical stimulation in the back. This approach involves an electrical stimulation device including at least one electrode adapted for insertion within an animal body with back pain and at least one pulse generator operatively coupled with the at least one electrode, wherein the pulse generator delivers electrical stimulation activating at least a nerve innervating at least a paraspinal muscle in a back of the animal body for pain relief.

24 Claims, 20 Drawing Sheets

(56) References Cited

U.S. PATENT DOCUMENTS

| | | |
|---|---|---|
| 8,626,302 B2 | 1/2014 | Bennett et al. |
| 8,700,177 B2 | 4/2014 | Strother et al. |
| 8,954,153 B2 | 2/2015 | Boggs, II |
| 2005/0240243 A1 | 10/2005 | Barolat et al. |
| 2006/0052826 A1* | 3/2006 | Kim .................... A61N 1/0558 607/2 |
| 2007/0027501 A1 | 2/2007 | Jenson et al. |
| 2008/0228241 A1 | 9/2008 | Sachs |
| 2010/0036454 A1 | 2/2010 | Bennett et al. |
| 2010/0152808 A1 | 6/2010 | Boggs, II |
| 2010/0152809 A1 | 6/2010 | Boggs, II |
| 2010/0241195 A1 | 9/2010 | Meadows et al. |
| 2011/0021943 A1 | 1/2011 | Lacour et al. |
| 2011/0224665 A1 | 9/2011 | Crosby et al. |
| 2012/0016439 A1 | 1/2012 | Alataris et al. |
| 2012/0290055 A1 | 11/2012 | Boggs, II |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2013/0096641 A1 | 4/2013 | Strother |
| 2013/0197615 A1 | 8/2013 | Rundle |
| 2013/0238066 A1 | 9/2013 | Boggs, II et al. |
| 2013/0296966 A1 | 11/2013 | Wongsarnpigoon et al. |

OTHER PUBLICATIONS

European Patent Office, Extended European Search Report for Application 13760774.3, PCT/US2013/032627, dated Jan. 5, 2016, 11 pgs., European Patent Office, Germany.

\* cited by examiner

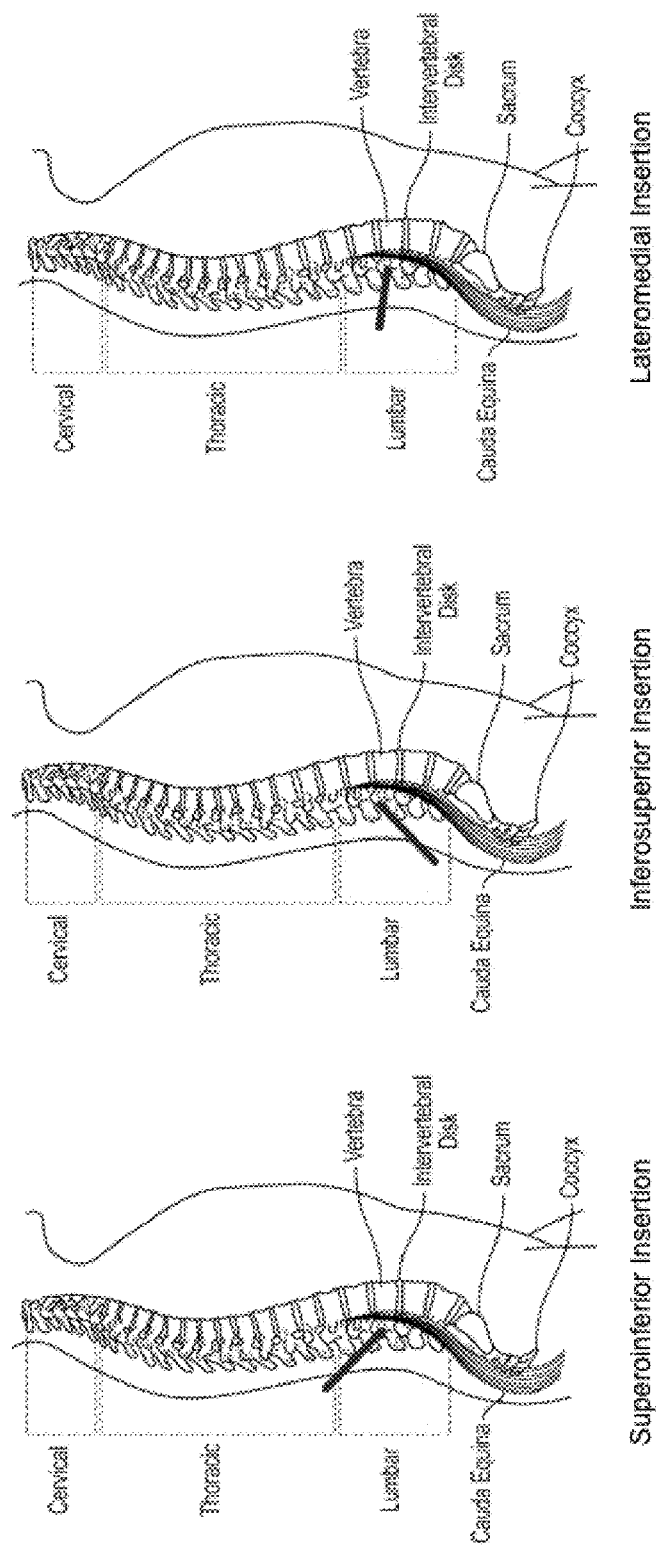

X= Electrode Location

X= Electrode Location

X= Electrode Location

SYSTEMS AND METHODS RELATED TO THE TREATMENT OF BACK PAIN

CROSS-REFERENCE TO RELATED APPLICATION

This application is a continuation-in-part of co-pending U.S. patent application Ser. No. 13/843,002 entitled "Systems and Methods Related to the Treatment of Back Pain" filed on Mar. 15, 2013, which claimed the benefit from U.S. Provisional Patent Application Ser. No. 61/611,560 entitled "Systems and Methods Related to the Treatment of Back Pain" filed on Mar. 15, 2012, both of which are hereby incorporated in its entirety by reference. This application also claims the benefit from U.S. Provisional Patent Application Ser. No. 62/084,727 entitled "Motor Nerve Stimulation as Treatment for Chronic Low Back Pain" filed on Nov. 26, 2014, which is hereby incorporated in its entirety by reference. This application also claims the benefit from U.S. Provisional Patent Application Ser. No. 62/091,613 entitled "Motor Nerve Stimulation as Treatment for Chronic Low Back Pain" filed on Dec. 14, 2014, which is hereby incorporated in its entirety by reference.

FIELD OF USE

The present application generally relates to a system and a method to deliver percutaneous stimulation to relieve pain and improve function in patients with back pain.

BACKGROUND

Back pain (e.g., chronic low back pain) affects approximately 30 million people in the U.S. and is the second leading cause of adult disability, which affects approximately 7 million people. Chronic back pain interferes with function, reducing activities of daily living, such as walking, housework, and personal care, and decreases quality of life. In addition, back pain is expensive to treat and leads to reduced productivity and ~150 million missed work days/year, resulting in total costs of ~$100-200 billion/year in the U.S. Further, back pain (e.g., low back pain) has a global prevalence of approximately 12% and is likely to increase substantially in the future as the population ages. Chronic back pain is distinct from acute back pain, commonly nonspecific and challenging to treat. While acute back pain (defined as pain lasting 3-6 weeks) may resolve on its own, pain recurrences are common after the initial episode of acute back pain and ~20% of people affected by acute back pain will develop chronic back pain. Chronic low back pain (characterized as lumbar pain lasting for ≥12 weeks), for example, is typically associated with greater pain intensity scores and bilateral axial pain (as opposed to unilateral or radiating pain). Although pain may originate from anatomical lesions (e.g., herniated intervertebral discs) or damage to soft tissues (e.g., muscles), chronic back pain is nonspecific (unknown cause of pain) in up to 85% of cases. Further, back pain may persist long after injuries to the back heal, making treatment futile with therapies that focus on the initiating cause or transmission of pain signals (instead of targeting the reversal of central pain sensitization for pain relief).

Present treatments for back pain (e.g., chronic and/or acute back pain) are often ineffective, not well tolerated and/or associated with side effects and complications.

Common analgesic medications (e.g., acetaminophen, NSAIDs, muscle relaxants, tricyclic antidepressants, corticosteroids) provide short-term pain relief and commonly produce undesirable side effects (e.g., sedation, gastrointestinal problems). Although analgesics can provide substantial pain relief in some, a large proportion of patients do not experience sufficient pain relief. Further, long-term use is not recommended, e.g., to prevent opioid dependence.

Injections of steroids or anesthetics or radiofrequency (RF) ablation provide short-term pain relief (on the order of a few months), but require frequent re-treatment sessions and are associated with side effects and complications (e.g., increased pain, lightheadedness, headache, infection, and nausea and vomiting). Intrathecal drug delivery is effective for reducing pain and improving function long-term but requires an invasive procedure and long-term implant and is limited by frequent side effects and technical complications that may require reoperation or removal of the device.

Alternative therapies, such as exercise, yoga, or strength training can be effective, but patients often fail to comply with treatment regimens.

Physical manipulation has a low level of risk and can provide short-term pain relief, but requires frequent treatment sessions. Acupuncture is a minimally-invasive procedure and studies have suggested that acupuncture can provide pain relief and improvements in function, but the effectiveness of acupuncture remains controversial. Surgical procedures for back pain (spinal fusion, disc replacement) are highly invasive and complex, irreversible, carry risks of complications, and seldom reduce pain or improve function. Further, reoperation is frequently required for failed back pain surgeries (up to 32%).

Existing methods of electrical stimulation reduce pain by generating paresthesias (i.e., tingling sensations) overlapping the regions of pain. Pain relief using these existing methods persists only for a short time following treatment, suggesting that chronic pain has not been reversed and/or the sensitization of central pain processing has not been addressed. As a result, only a small percentage of patients using existing methods of electrical stimulation experienced clinically significant reductions in chronic back pain post-treatment. Transcutaneous electrical nerve stimulation (TENS) and spinal cord stimulation (SCS) have been investigated for the treatment of chronic back pain and neither provides a suitable option for reliable, effective relief of some types of chronic back pain.

TENS is a non-invasive method to deliver electrical stimulation through surface electrodes to generate paresthesia coverage of the regions of pain. TENS requires frequent treatment sessions to maintain pain relief, but consistent efficacy in chronic back pain has not been demonstrated. Although TENS can be self-administered at home, TENS systems can be cumbersome and not practical for daily use. Also, TENS can activate cutaneous fibers and cause irritation and discomfort, limiting the maximum tolerable stimulation intensity and treatment duration that can be delivered and reducing the potential efficacy of the treatment. TENS, while non-invasive, lacks evidence of effectiveness for chronic back pain and may produce discomfort from stimulation of cutaneous fibers.

Spinal cord stimulation is a method to deliver electrical stimulation through implanted leads connected to an implanted pulse generator to generate paresthesia coverage of the regions of pain. SCS is invasive, associated with device complications and less effective for non-radicular pain. Spinal cord stimulation requires complex and invasive surgery to implant the leads and pulse generator. Spinal cord stimulation has a moderate rate of complications, including additional pain and hardware complications, and as a result, revision surgery, reprogramming, or removal of the stimulator is often required.

In summary, present treatments for chronic back pain seldom provide adequate long-term relief of pain or improvements in function; carry risks of side effects and complications; and/or are invasive.

There remains room in the art of pain management for alternative systems and methods to be used in the treatment of back pain (e.g., chronic low back pain).

SUMMARY

Embodiments according to the present application provide improved systems and methods to be used to assist in the treatment of back pain.

The present application provides an electrical stimulation device having at least one lead adapted for insertion within an animal body with back pain and at least one pulse generator operatively coupled with the at least one electrode, wherein the pulse generator delivers electrical stimulation activating at least one nerve (e.g., dorsal ramus and/or other nerves, nerve trunks, or nerve branches in the back) to activate at least one muscle in a back of the animal body for pain relief.

The present application also provides an electrical stimulation system including an electrical stimulation device having at least one electrode adapted for insertion below the skin of an animal body with back pain and a pulse generator operatively coupled with at least one electrode, wherein the pulse generator delivers electrical stimulation for a prescribed period of time to activate at least one nerve (e.g., afferent or efferent nerve fibers) near the dorsal ramus to activate at least one muscle in a back of the animal body for pain relief. The electrical stimulation device may be operatively coupled to an external stimulator operatively coupled to an external controller.

The present application further provides a method to alleviate back pain including placing at least one electrode within a tissue of an animal body, and applying stimulation through the at least one electrode to activate at least one nerve near the dorsal ramus to activate at least one muscle in a back of the animal body for pain relief.

In an embodiment, the method includes modulating central neural processing through the activation of the nerve near the dorsal ramus of the animal body. The method may include activating at least one paraspinal muscle of the animal body through the activation of the at least one nerve near the dorsal root of the animal body. The activation of the paraspinal muscle may not affect the strength of the paraspinal muscle.

The method may also produce an increase in stimulation-evoked neural encoded signals. The method may also produce a change in afferent and/or efferent nerve activity.

The method may also include evaluating an area of back pain, positioning, repositioning, and stimulating the electrode. The method may result in the alleviation of back pain after the stimulation is discontinued.

In one embodiment, the method may further include the insertion of additional electrodes, stimulating the additional electrodes and comparing the results. The method may also include the removal of the original electrode and use of the additional electrodes.

Other features and advantages of the present applications are set forth in the following specification and attached drawings.

BRIEF DESCRIPTION OF THE DRAWINGS

Operation of the invention may be better understood by reference to the detailed description taken in connection with the following illustrations, wherein:

FIGS. 5A-5C is three different side views of the insertion of a lead into an animal body;

DETAILED DESCRIPTION

Figure 1:
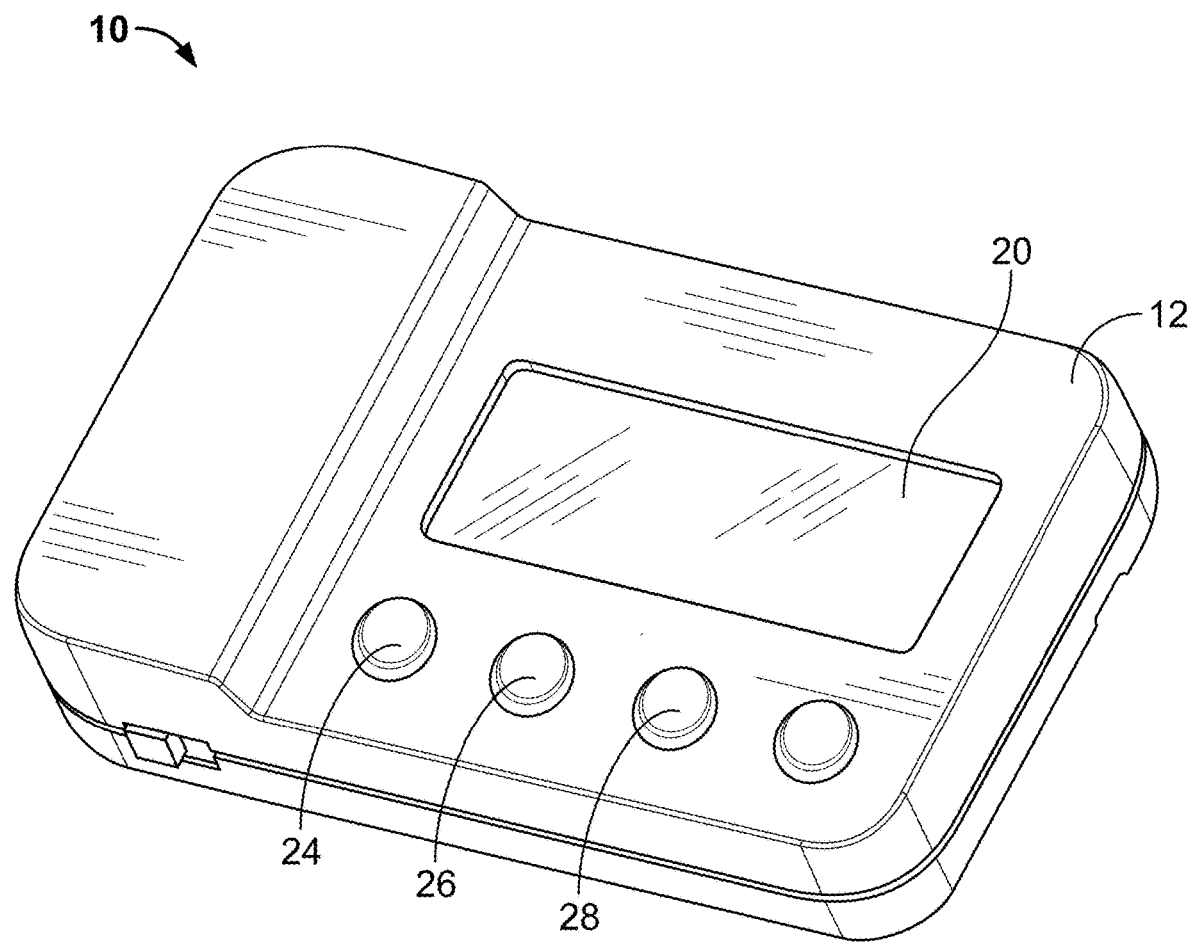
FIG. 1 is a frontal view of a stimulation pulse train generator.

Reference will now be made in detail to exemplary embodiments of the present technology, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination.

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

The stimulation system discussed below involves inserting an electrode into an animal body and using electrical stimulation to activate nerve(s) to provide pain relief. Any method of electrical stimulation will work to activate at least one nerve in the body. In one embodiment, the stimulation system activates peripheral or spinal nerves in a way that produces the activation of muscles, which generate neurally encoded signals in the afferent fibers innervating the paraspinal muscles (e.g., multifidus, erector spinae, longissimus, iliocostalis, etc.) of the back, such that the neurally encoded signals may modulate central processing of pain.

The present system may activate peripheral or spinal nerves (e.g., efferent nerve fibers) in a way that produces activation of muscles, which generate neurally encoded signals in the afferent fiber(s) innervating the paraspinal muscle(s) of the back, such that the neurally encoded signals may modulate central processing of pain. Sustained pain relief is critical to produce substantial impacts on patient's quality of life and improve function, and may be accomplished by eliminating the source of painful signals and/or addressing problems in the central pain processing system that yield chronic pain. The system is designed to produce modulation of central pain processing such that the perception of pain is reduced or eliminated and this reduction or elimination of pain can outlast the duration of the stimulation of the peripheral or spinal nerve. In one embodiment, the present system enables this modulation of central pain processing to be produced with the use of the self-anchoring electrode and/or lead that can be temporarily placed through a simple and/or minimally-invasive percutaneous insertion, avoiding the need to permanently place an electrode or lead with surgery. It is to be appreciated that the same effect and method may also be accomplished by more invasive means such as surgery, but this system may enable the activation of nerves to produce pain relief in a way that avoids and/or does not require surgery. As a non-limiting example, stimulation of peripheral nerves (e.g., dorsal ramus, spinal nerve) with the present system can produce neural activation in a way that can contract and/or relax muscle(s) comfortably and repeatedly (e.g., cyclically, intermittently, and/or regularly) to desirably generate (e.g., produce, propagate) neural signals in afferent fibers in a nerve that produce changes in central processing of pain (e.g., in the central nervous system (CNS), such as the spinal cord, brain, and/or other central neural processing centers).

This system may enable the activation of peripheral, spinal nerves and/or their branches and may generate activation of paraspinal muscles, which may be widespread, limited, or desirably controlled to the appropriate and/or therapeutic regions or levels most effective in generating neurally encoded signals in afferent nerve fibers to evoke changes in central processing of pain. Activation of muscles by nerve stimulation and the generation of neurally encoded afferent signals can modulate neural processing of nociceptive inputs and alter pain processing. By targeting the peripheral nerves (e.g., spinal nerve, dorsal ramus, distal branches, etc.), this type of stimulation may produce widespread and/or controlled activation of motor fibers (e.g., across multiple muscles and/or spinal levels or segments) and may generate an increased amount (e.g., number, intensity, duration, etc.) of afferent nerve signaling that may modulate central pain processing, avoiding the need to place multiple electrodes and/or leads to produce widespread activation of muscles in the region of pain. However, contraction of muscles may be evoked using electrical stimulation in many possible ways. Electrical stimulation may be used to activate motor axons in the nerve (e.g., at the dorsal ramus or peripheral nerves), at motor points of muscles, where motor axons enter a muscle, or activate the muscle directly (e.g., without activation of the motor axons). However, threshold stimulation intensities for activation of motor axons may typically be lower than that of direct activation of muscle. Electrical stimulation may also be used to stimulate other parts of the body to cause a reflex response that activates the target muscle. Stimulation may also be used to activate muscle by stimulation of the dorsal ramus of spinal nerve, ventral ramus of spinal nerve, dorsal root ganglion, spinal nerve, and/or the spinal cord. Stimulation may also be used to activate nerves that produce activation of a structure that is not in the back (e.g., an abdominal muscle, a shoulder muscle, etc.) that may cause passive movement (e.g., stretching, compression, torsion) of a back muscle. The selection of peripheral nerves as the stimulation target is an improvement over the current methods of targeting muscles and/or motor points in the muscles with stimulation, as the present approach may produce widespread motor activation in addition to simplifying the procedure for placement of electrodes and/or leads by minimizing number of leads required to produce activation of paraspinal muscles in the region of pain and avoiding need to reposition needles and/or electrodes multiple times.

The present system may produce activation of nerves and paraspinal muscles that may reduce pain or the perception of pain without requiring strengthening of paraspinal muscles. Stimulation of nerves and muscles may produce activation of neural pathways that influence the perception, processing and/or generation of pain signals and the goal of stimulation is to activate those pathways to restore normal or improved pain processing. The present system may enable the modulation of central pain processing via the stimulation of peripheral nerves and activation of paraspinal muscles, however this generation of afferent signals that may modulate central processing does not require that muscles be strengthened. In contrast to other therapies, the strengthening of paraspinal muscles (e.g., increase in the size, or change in the shape, composition or endurance of muscle) is not required for pain relief, as stimulation to activate muscle fibers generates neurally encoded afferent signals, which may modulate central pain processing, irrespective of the strength of muscles. Therefore, the present system may enable the stimulation of nerve fiber(s) in peripheral nerves producing changes in central pain processing (e.g., brain, spinal cord, and/or other central neural processing centers) to modulate the perception of pain, without requiring that significant changes be manifested in the muscles themselves. In another embodiment, pain may be reduced without providing mechanical strengthening, and although mechanical strengthening may occur, it is not required as part of the present system. As an additional example, the present system may enable the modulation of central pain processing via the stimulation of peripheral nerves and activation of paraspinal muscles, and the modulation of pain processing and/or modulation of pain (e.g., conveyance of pain relief) may be provided prior to or without requiring functional improvement (e.g., modulation of pain processing and/or pain relief may be provided in a patient with back pain prior to or without providing functional improvement, changes in muscle strength, stability, flexibility, and/or other mechanical or functional outcomes). Such changes may occur, but they are not required for the present system to modulate pain processing. As an example, the present system may modulate neural processing without altering function.

Furthermore, this system may enable pain relief by stimulation of peripheral nerves and activation of central pain processing via generation of afferent signals without requiring stabilization of the spine, musculature or connective tissues (e.g., tendons, ligaments, etc.). Stimulation and activation of musculature may generate neurally encoded signals that relieve pain and/or modulate pain signal processing unrelated to the stability or status of bones, musculature or connective tissue. Thus, the present system presents an advantage over the prior art; as this system enables activation of peripheral nerves and paraspinal muscles that generate afferent signals to modulate central pain processing, enabling reductions in pain prior to or without mechanical stabilization. Further, this system avoids targeting or generating changes in stability of the spine, musculature or connective tissues, and provides pain relief through central pain processing. In another embodiment, pain can be reduced without providing mechanical stability, and although mechanical stability may occur, it is not required as part of the present system.

The present system provides a method of activation of nerves that enables changes in central nervous system processing in such a way that can outlast the duration of therapy (e.g., on short term and/or long term). Modulation of central spinal processing brought about by activation of paraspinal muscles, which may be activated by peripheral nerve stimulation and can outlast stimulation of the nerves that produced contraction of the muscles on the short term (e.g., second, minutes and/or days) or long term (e.g., days, weeks, months and/or years) after stimulation stops being applied to nerves. This sustained therapeutic benefit offers an advantage over the prior art and existing therapies, where continuous or long-term intermittent stimulation is required to produce pain relief, and/or sustained, lasting benefit (e.g., relief of pain or improvement in function) cannot be achieved after terminating the therapy. Furthermore, the present system may present an advantage of the prior art, as this long-lasting modulation of central pain processing may be accomplished with a system that is minimally-invasive (e.g., percutaneous electrode insertion), temporary (e.g., short-term therapy administered over a period of weeks), safe (e.g., coiled lead design has negligible risk of infection or device-related adverse events) and reliable (e.g., self-anchoring lead prevents lead migration, ensuring comfortable, uninterrupted therapy). As a further example, the present system may enable a short-term therapy (e.g., a temporary percutaneous system using a percutaneous lead coupled to an external stimulator) to provide long-term pain relief (e.g., by modulation of central pain processing).

This system may address the underlying source of dysfunction that is responsible for back pain (e.g., chronic low back pain). The goal of the invention is to treat or reverse the occurrence of pain without requiring repair and/or treatment of the initiating cause of low back pain (e.g., injury, structural deformity, or disease). Furthermore, this system provides an effective method to treat back pain that can avoid the use of multiple, separate therapies, which individually target the original injury or cause of pain and/or fail to correct the central problem of pain processing. With this system, modulation of central pain processing may be activated through stimulation of peripheral nerve fibers (e.g., afferent or efferent) and/or activation of paraspinal muscles, which in turn produce afferent neural signals. The central modulation of spinal pain processing with this system, as a result of stimulation of peripheral nerves, allows for treatment of low back pain by altering the central neural nociceptive processing preventing pain sensation. Unlike other therapies and prior art (e.g., physical therapy, TENS, back brace, and prior methods of neuromuscular stimulation), which target original source of pain (e.g., restoring stability to instable structures, regions, muscles, and/or components of the back, strengthening weakened structures, regions, muscles, and/or components of the back), this method enables directed treatment of the present source of the pain (e.g., the central processing of neural inputs, which can affect the modulation, processing, and/or perception of pain). This invention avoids unintentional discomfort from exacerbation of pain from treatments targeting peripheral structures (e.g., TENS, physical therapy, and other forms of stimulation). Furthermore, in one embodiment, this system may be used to enable pain relief resulting from various causes of pain, via activation of peripheral nerves and paraspinal muscles and modulation of central pain processing.

Because the present system, can deliver stimulation, generate muscle contractions that are comfortable, and avoid causing discomfort, the present system can avoid the need to provide additional analgesic stimulation to relieve discomfort caused by the therapeutic stimulation and/or muscle contractions (i.e., the present system may be effective while avoiding causing discomfort). This system may provide a clinically meaningful an advantage over previous methods of treating back pain that could not reliably prevent stimulation from causing discomfort and/or muscle contractions that caused discomfort and required methods to relieve the iatrogenic discomfort or pain that could accompany the therapy. For example, because the present system may not require (e.g., avoids and/or avoids the need for) stimulation of muscles at a level (e.g., intensity, frequency, duration, and/or other parameter setting) necessary to cause functional changes, such as strengthening, stability, which may require uncomfortable muscle contractions, it may avoid delivering painful stimulation and/or avoids other painful responses, such as painful or uncomfortable, muscle contractions, and delivers non-painful stimulation that comfortably contracts and/or relaxes muscle in a way that generates neurally encoded signals in afferent nerve fibers that modulate central pain processing, reducing the perception of pain. Furthermore, the pain relief produced by the invention may outlast the duration of stimulation provided by the invention due to the modulation or resetting of the central pain processing center(s), enabling a temporary system to provide long term relief of back pain.

With reference to FIG. 1, a percutaneous stimulation system is shown that can be used with the method of treating the back in accordance with the present teachings. The stimulator may include an electrical stimulation pulse generator 10. The pulse generator 10 may include a lightweight, durable housing 12 that may be fabricated from a suitable plastic or the like. In some embodiments, the case 12 may include a clip that allows the pulse generator 10 to be releasably connected to a patient's belt, other clothing, or any other convenient location. The case 12 may also include a releasable battery access cover. Other means of securing the stimulator may be used that allow the stimulator to be secured to the patient's skin without and/or under clothing (e.g., adhesive, magnet, etc.).

For output of data to a patient or clinician operating the stimulation system, a visual display 20 may be provided. The display 20 may be by a liquid crystal display, but any other suitable display may alternatively be used. An audio output device, such as a beeper may also be provided. Alternatively, data may be conveyed to the user in other ways (e.g., tactile, flashing LEDs).

For user control, adjustment, and selection of operational parameters, the stimulation pulse generator 10 may include a mechanism or device for input of data. The pulse generator 10 may include an increment switch 24, a decrement switch 26, and a select or "enter" switch 28. The increment and decrement switches 24, 26 may be used to cycle through operational modes or patterns and stimulation parameters displayed on the display 20, while the select switch 28 may be used to select a particular displayed operational pattern or stimulation parameter. The select switch 28 may also act as a power on/off toggle switch.

For output of electrical stimulation pulse train signals, the pulse train generator 10 may include an external connection socket (not shown) that may mate with a connector of an electrode cable assembly (not shown) to interconnect the pulse generator 10 with a plurality of electrodes, such as through use of percutaneous electrode leads. More particularly the cable assembly connected to the socket 30 may include a second connector such as on a distal end that may mate with a connector attached to the proximal end of each of the percutaneous stimulation electrode leads and a reference electrode lead. Alternatively, the pulse generator may transmit signals without a physical connection to the electrode (e.g., radio-frequency coupling, passive polarization of electrode) or may be housed within a single unit along with the electrode.

Figure 2:
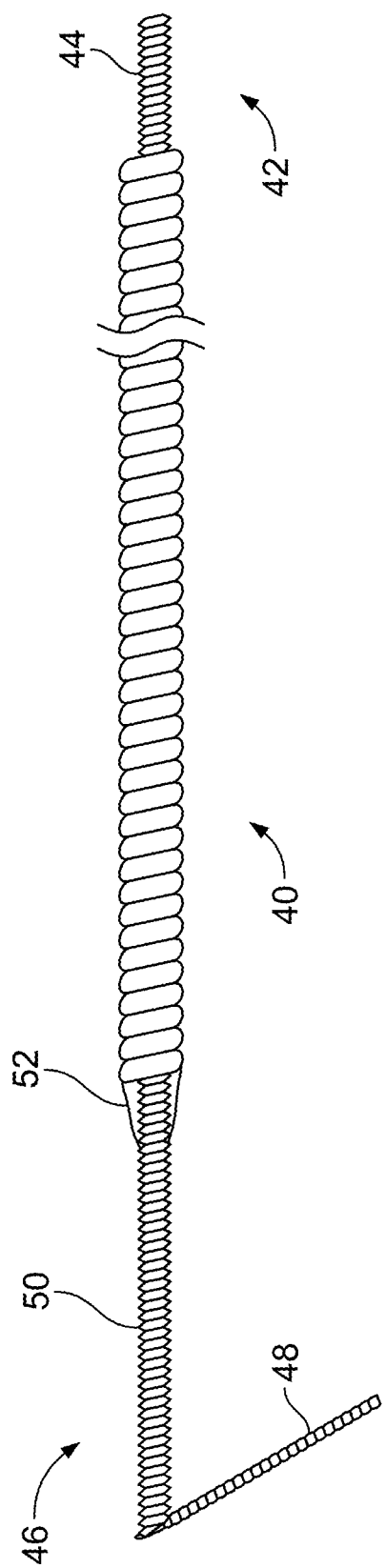
FIG. 2 is a top view of an electrode and percutaneous electrode lead.

Exemplary embodiments of an electrode and percutaneous lead are shown in FIG. 2. The electrode lead 40 may be fabricated from a 7-strand stainless steel wire insulated with a biocompatible polymer. Each individual wire strand may have a diameter of approximately 34 μm and the insulated multi-strand lead wire may have a diameter of approximately 250 μm. It should be understood, however, that these dimensions are merely exemplary and the present teachings are not limited to such. Any appropriate sized, shaped and configured electrode and percutaneous lead may be used. The insulated wire may be formed into a spiral or helix as has been found to accommodate high dynamic stress upon muscle flexion and extension, while simultaneously retaining low susceptibility to fatigue. The outer diameter of the helically formed electrode lead 40 may be approximately 580 μm and it may be encased or filled with silicone or the like. Alternatively, the lead may have additional or fewer strands, may be made out of a different material (e.g., another metal, conducting polymer), may be insulated with another material, or may not be insulated. Further, the lead may be the same type of use for spinal cord stimulation (e.g., cylindrical or paddle-type leads).

As mentioned above, a proximal end 44 of each of the plurality of electrode lead wires 40 may be located exterior to the patient's body when in use. The proximal end 44 may include a deinsulated length for connection to an electrical connector in combination with the remainder of the electrode leads. The deinsulated portion may be located on any portion of the proximal portion of the lead located outside of the body. In some embodiments, the distal end 46 of each lead 40, which may be inserted directly into tissue, may also include a deinsulated length. The deinsulated length may act as the stimulation electrode 50. At least a portion of the deinsulated length may be bent or otherwise deformed into a barb 48. This may anchor the electrode in the selected tissue. A taper 52, made from silicone adhesive or the like, may be formed between the deinsulated distal end 50 and the insulated portion of the lead 40 to reduce stress concentration. The electrode may be placed anywhere along the length of the lead; the present teachings are not limited to the aforementioned locations. The electrode may be a conductive contact connected (e.g., welded, via adhesive) to the lead. Alternatively, the lead may be threaded (i.e., like a screw), and may be inserted into the tissue (e.g., pushed, deployed, screwed, etc.), which will mechanically secure the lead in the tissue.

Unlike surface electrodes that are applied to the surface of the patient's skin using an adhesive, each of the plurality of percutaneous electrodes 50 may be surgically implanted or otherwise inserted into select patient's tissue. The associated electrode lead 40 may exit the patient percutaneously, i.e., through the skin, for connection to the stimulation pulse generator 10. Each of the electrodes 50 may be implanted or otherwise inserted into the select tissues by use of a needle. The needle may be straight or may be hooked. Alternatively, the lead may be inserted using other hollow tubes (e.g., cannula, catheter) or may be "shot" out of a device at sufficiently high speeds such that a rigid structure (e.g., needle) is not needed to penetrate the skin. Alternatively, the lead may be introduced through a vessel (e.g., vein, artery). Alternatively, the lead itself may be rigid, enabling the lead to be insertable into the tissue without another object (e.g., a needle). Alternatively, or in addition, tissues may be surgically exposed for implantation or minimally invasive techniques such as arthroscopy may be used. Alternatively, multiple electrodes may be on an array (e.g., paddle electrode, cylindrical electrode, array of needles, etc.). Once all of the electrodes are implanted as desired, their proximal ends may be crimped into a common connector that may mate with the cable assembly. The cable assembly may be, in turn, connected to the pulse generator 10 through the connection socket 30. Alternatively, the electrodes may be connected directly to the stimulator. Alternatively, each electrode may be connected to an individual connector. Alternative means of securing the leads to the connector may also be used (e.g., magnetic, adhesive). Alternatively, the proximal ends of the leads may terminate on a plug (e.g., banana plug, BNC plug) that can be connected to the stimulator either directly or via a connector. Such therapies or uses may require multiple systems, which utilize multiple pulse train generators with multiple common connectors.

The present percutaneous stimulation system may allow for precise selection of nerve stimulation and use of two or more stimulation electrodes and channels. Alternatively, a system may use one stimulation electrode. The system in accordance with the present technology may use two or more electrodes 50, each connected to an independent electrode stimulation channel E, and a single reference electrode 52 that may be a percutaneous, surface electrode, the case of the stimulator (if implanted), or an implanted electrode. Alternatively, there may be more than one reference electrode, and each stimulation channel may have its own reference electrode. The electrode stimulation channels may not be independent, i.e., the same stimulation may be delivered to multiple channels at once.

The stimulation pulse generator 10 may include a microprocessor-based stimulation pulse generator circuit with a micro controller such as a Motorola 68HC12. Operational instructions or other information may be stored in nonvolatile storage. Set stimulation therapy or patterns may be included in this storage. These therapies may be based upon generalized information such as information that may be gathered from radiographic evaluation in multiple dimensions along with selected stimulation. Ultimately patient specific information may be incorporated into the stimulation parameters in order to optimize the therapy for a particular individual application. Preferably, the nonvolatile memory may also provide storage for all patient-specific stimulation protocols. A real time clock may be provided as part of the circuit.

The electrical stimulator current may pass between the selected electrodes and the reference electrode(s). A pulse duration timer may provide timing input PDC as determined by the CPU to the pulse amplitude/duration controller to control the duration of each stimulation pulse. Likewise, the CPU may provide a pulse amplitude control signal to the circuit by way of the serial peripheral interface to control the amplitude of each stimulation pulse.

Each output channel E1-E2 may include independent electrical charge storage such as a capacitor SC that is charged to the high voltage VH through a respective current limiting diode CD. To generate a stimulation pulse, the microcontroller output circuit 102 may provide channel select input data to switch component, as to the particular channel E1-E2 on which the pulse may be passed. Switch SW may close the selected switch SW1-SW2 accordingly. The microcontroller may also provide a pulse amplitude control signal PAC into a voltage-controlled current source VCCS. As such, the pulse amplitude control signal PAC may control the magnitude of the current I, and the circuit VCCS may ensure that the current I is constant at that select level as dictated by the pulse amplitude control input PAC. For stimulation of human nerve (e.g., motor axons in peripheral nerve), the current I may be within an approximate range of 0.1 mA-100 mA, or even 1 mA-20 mA. However, the present teachings are not limited to such range. Any appropriate range may be used with the present teachings.

Upon completion of the cathodic phase Qc as controlled by the pulse duration control signal PDC, the discharged capacitor SC may recharge upon opening of the formerly closed one of the switches SW1-SW2. The flow of recharging current to the capacitor SC may result in a reverse current flow between the relevant electrode 50 and the reference electrode 52, thus defining an anodic pulse phase Qa. The current amplitude in the anodic pulse phase Qa is limited, preferably to 0.5 mA, by the current limiting diodes CD. Of course, the duration of the anodic phase may be determined by the charging time of the capacitor SC, and current flow may be blocked upon the capacitor becoming fully charged. It should be recognized that the interval between successive pulses or pulse frequency PF may be controlled by the CPU 62 directly through output of the channel select, pulse amplitude, and pulse duration control signals as described at a desired frequency PF.

Some embodiments may implement (e.g., from 1 to 8 or more) independent preprogrammed patterns. For each pattern, a stimulation session S may be pre-programmed into the stimulator circuit by a clinician through use of the input device. Each session S may have a maximum session duration of approximately 24 hours, and a session starting delay D. However, it should be understood that these parameters are merely exemplary and not exhaustive or exclusive.

Figure 3:
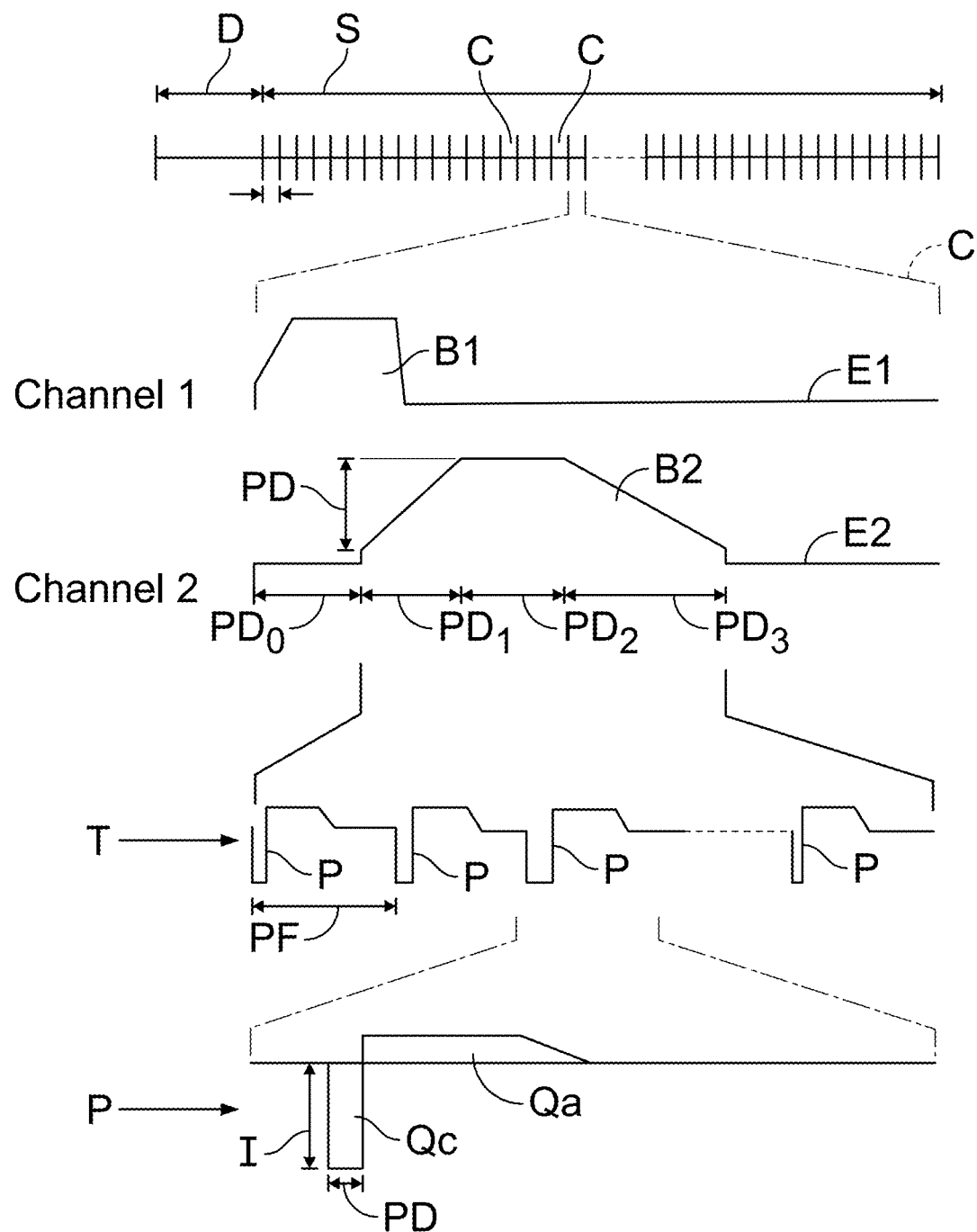
FIG. 3 graphically illustrates the stimulation paradigm of a percutaneous stimulation system.

With continuing reference to FIG. 3, a stimulus pulse train T may include a plurality of successive stimulus pulses P. A stimulus pulse P may be current-regulated. It may also be biphasic, i.e., comprises a cathodic charge phase Qc and an anodic charge-phase Qa. Alternatively, the stimulus pulse may be monophasic, i.e., comprises only a cathodic charge phase or anodic charge phase, or contain more than 2 phases. The magnitude of the cathodic charge phase(s) Qc, may be equal to the magnitude of the anodic charge phase(s) Qa. The current-regulated, biphasic pulses P may provide for consistent muscle recruitment along with minimal tissue damage and electrode corrosion. Alternatively or in addition to, a stimulus pulse may be regulated by other parameters (e.g., voltage-regulated, charge-regulated).

Each pulse P may be defined by an adjustable current I (or voltage for voltage-regulated, or charge for charge-regulated, etc.) and an adjustable pulse duration PD. The pulse frequency PF may also be adjustable. Further, the current I, pulse duration PD, and pulse frequency PF may be independently adjustable for each stimulation channel E. The amplitude of the anodic charge phase Qa may be fixed, but may be adjusted if desired.

Pulse "ramping" may be used at the beginning and/or end of each stimulation pulse train T to generate smooth muscle contraction, but other methods may be used as well. Ramping is defined herein as the gradual change in cathodic pulse charge magnitude by varying at least one of the current I and pulse duration PD. In FIG. 3, an embodiment of a ramping configuration is illustrated in greater detail. As mentioned, each of the plurality of stimulation leads/electrodes 40, 50 may be connected to the pulse generator circuit 60 via a stimulation pulse channel E. As illustrated in FIG. 3, two stimulation pulse channels E1 and E2 may be provided to independently drive up to two electrodes 50. Stimulation pulse trains transmitted on each channel E1 and E2 may be transmitted within or in accordance with a stimulation pulse train envelope B1-B2, respectively. The characteristics of each envelope B1-B2 may be independently adjustable by a clinician for each channel E1-E2. Referring particularly to the envelope B2 for the channel E2, each envelope B1-B2 may be defined by a delay or "off" phase PD0 where no pulses are delivered to the electrode connected to the subject channel, i.e., the pulses have a pulse duration PD of 0. Thereafter, according to the parameters programmed into the circuit 60, the pulse duration PD of each pulse P is increased or "ramped-up" over time during a "ramp-up" phase PD1 from a minimum value (e.g., 5 μsec) to a programmed maximum value. In a pulse duration "hold" phase PD2, the pulse duration PD remains constant at the maximum programmed value. Finally, during a pulse duration "ramp-down" phase PD3, the pulse duration PD of each pulse P may be decreased over time to lessen the charge delivered to the electrode 50. Further, it is possible to "ramp-up" and "ramp-down" for zero seconds, which indicates that there is no ramping.

This "ramping-up" and "ramping-down" is illustrated even further with reference to the stimulation pulse train T which is provided in correspondence with the envelope B2 of the channel E2. In accordance with the envelope B2, the pulse P of the pulse train T first may gradually increase in pulse duration PD, then may maintain the maximum pulse duration PD for a select duration, and finally may gradually decrease in pulse duration PD.

As mentioned, the current I, pulse duration PD, pulse frequency PF, and envelope B1-B2 may be adjustable for every stimulation channel E, independently of the other channel. The waveform shape (e.g., rectangular, exponential, ramp; pre-pulse, post-pulse) and channel synchrony (i.e., when stimulation through each channel starts and stops with respect to the other channels) may also be adjustable. The stimulation pulse generator circuit 60 may be pre-programmed with one or more stimulation patterns, which may allow a patient to select the prescribed one of the patterns as required or otherwise desired during therapy. The pulse train, however, does not have to be constant (e.g., frequency may vary). Additionally, the ramping parameters may be adjusted (e.g., off time, ramp up time, ramp down time, and hold time).

In some embodiments, the pulse generator 10 may include at least two stimulation pulse channels E. The stimulation pulse trains T of each channel E may be sequentially or substantially simultaneously transmitted to their respective electrodes 50. The pulse frequency PF may be adjustable within the range of approximately 1 Hz to approximately 100 Hz; the cathodic amplitude PA may be preferably adjustable within the range of approximately 0.1 mA to approximately 100 mA; and, the pulse duration PD may be preferably adjustable in the range of approximately 1 μsec to approximately 500 μsec delivered by the circuit 60.

In alternative embodiments, the pulse generator may be implantable into a patient's body and would generate stimulation in a similar fashion as described previously for an external stimulator. In such embodiments, the pulse generator may be implanted in any appropriate location of a patient's body, including, without limitation, within the back, abdomen, legs, torso and the like. With an implantable pulse generator, both the generator and the electrodes (and leads, if applicable) may be placed underneath the skin. As a result, a programmer may communicate with the stimulator through the skin. Prior to placing the implantable pulse generator, a patient may use a percutaneous system as a trial.

Figure 4:
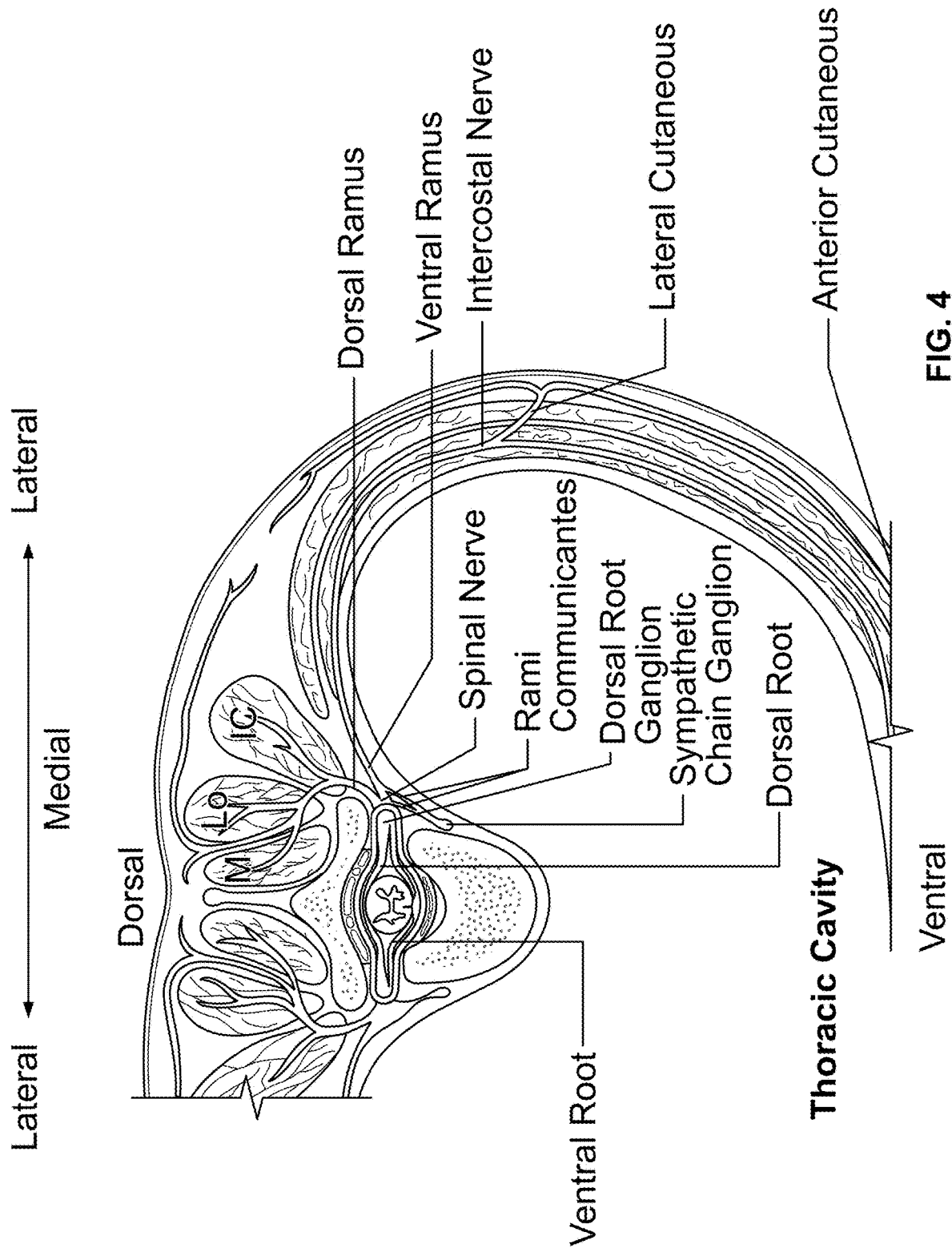
FIG. 4 is a cross-sectional view of the innervation of paraspinal muscles.
Figure 6C:
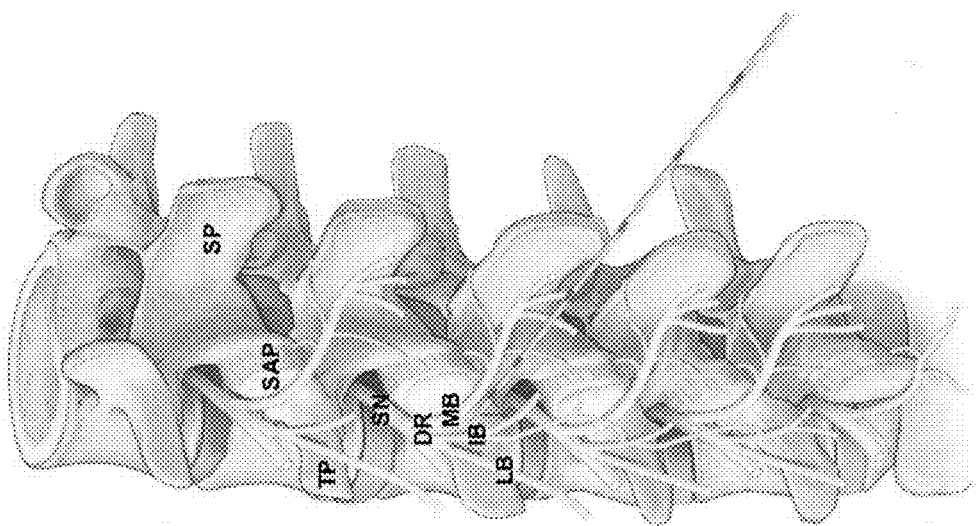
FIGS. 6A-6C is three different side views of the insertion of a lead into an animal body.
Figure 6B:
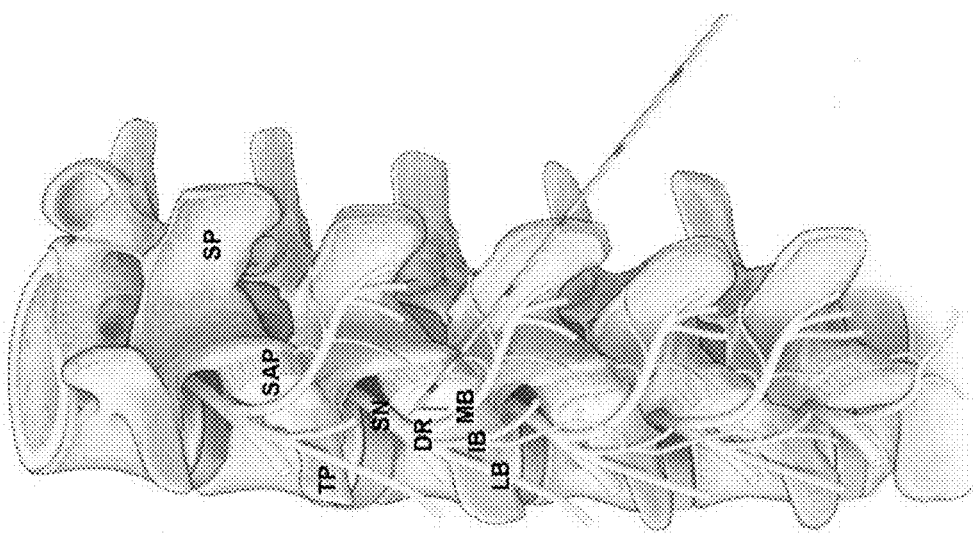
Figure 6A:
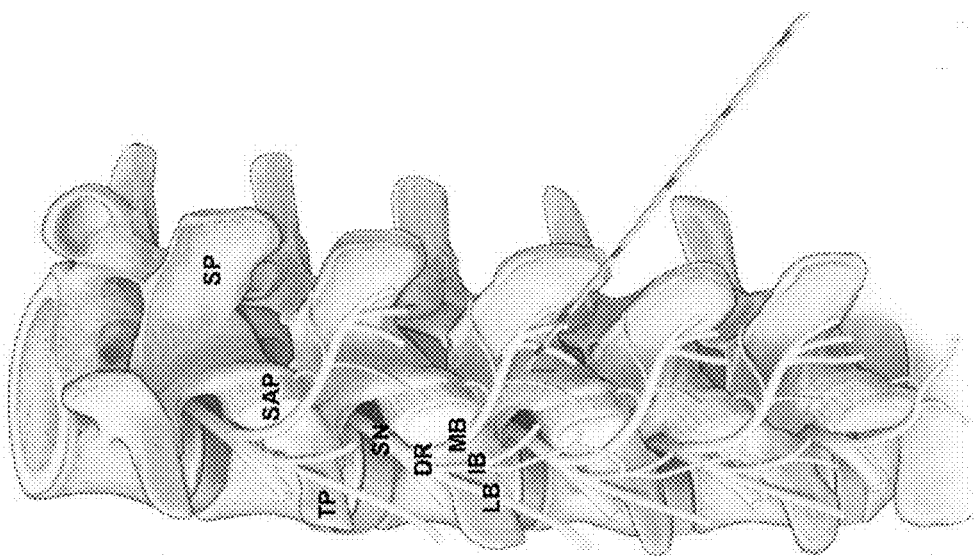
Figure 7A:
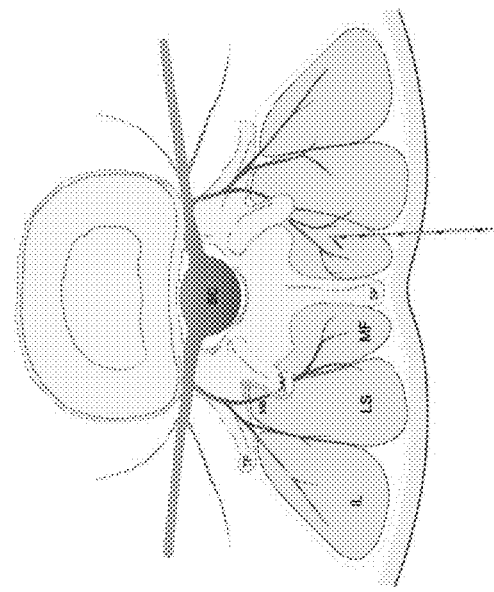
FIGS. 7A-7F is a cross-sectional view of the insertion of an introducer and lead into an animal body.
Figure 7D:
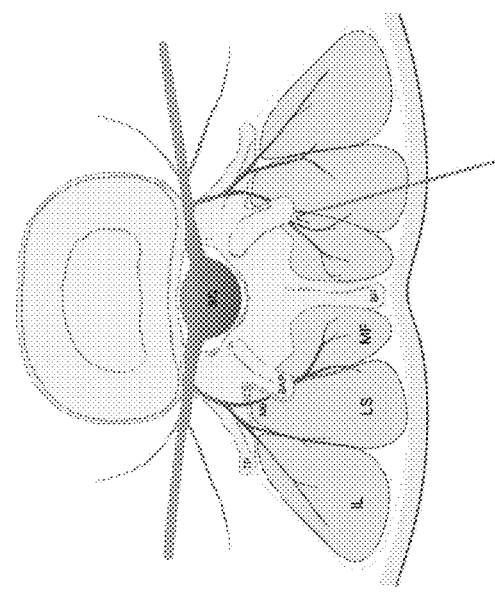
Figure 7B:
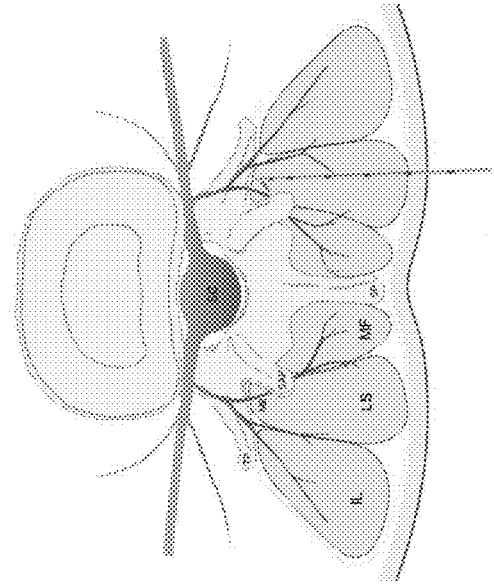
Figure 7E:
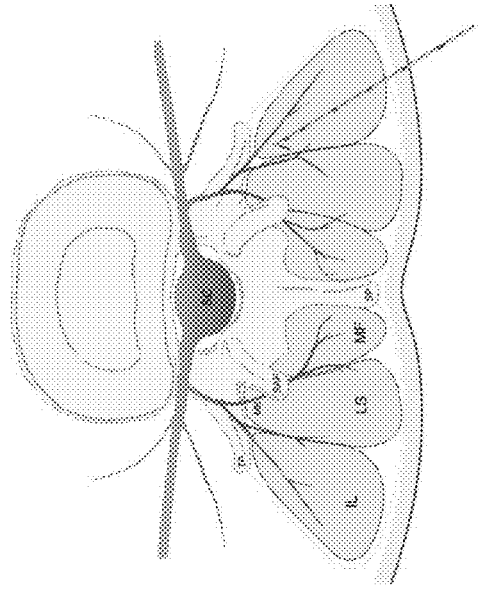
Figure 7C:
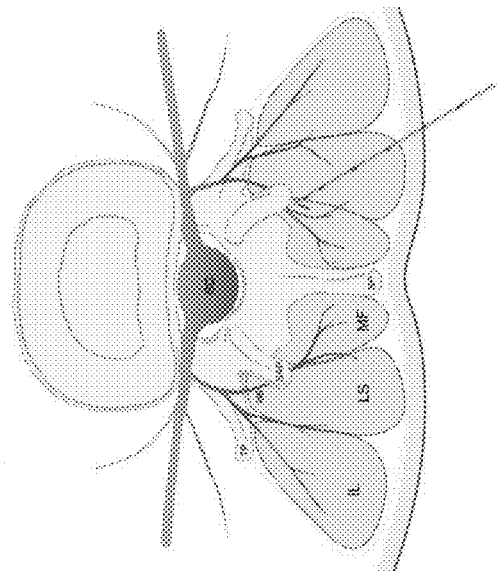
Figure 7F:
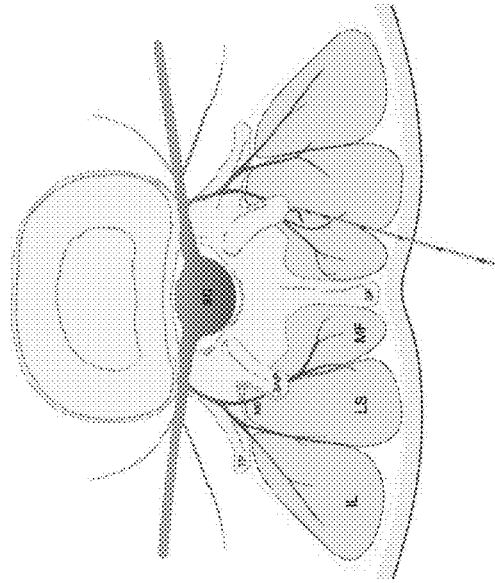

According to one method of treatment according to the present teachings, percutaneous leads may be placed to target the nerve(s) innervating paraspinal musculature (e.g., dorsal ramus, spinal nerve, distal branches, etc.) in the regions of back pain (see FIG. 4), although this approach may be generalized to any muscle in the back, including, but not limited to, multifidus, longissimus, iliocostalis, spinalis, latissimus dorsi, rhomboid, serratus posterior, oblique external, oblique internal, quadratus lumborum, psoas major, psoas minor, trapezius, levator scapulae, splenius capitis, splenius cervicis, semispinalis muscles, rotatores muscles, rectus capitis posterior muscles, interspinales, levatores costarum, obliquus capitis inferior muscle, obliquus capitis superior, rectus capitus posterior major, and rectus capitis posterior minor, and the leads may be placed in any tissue.

Figure 11:
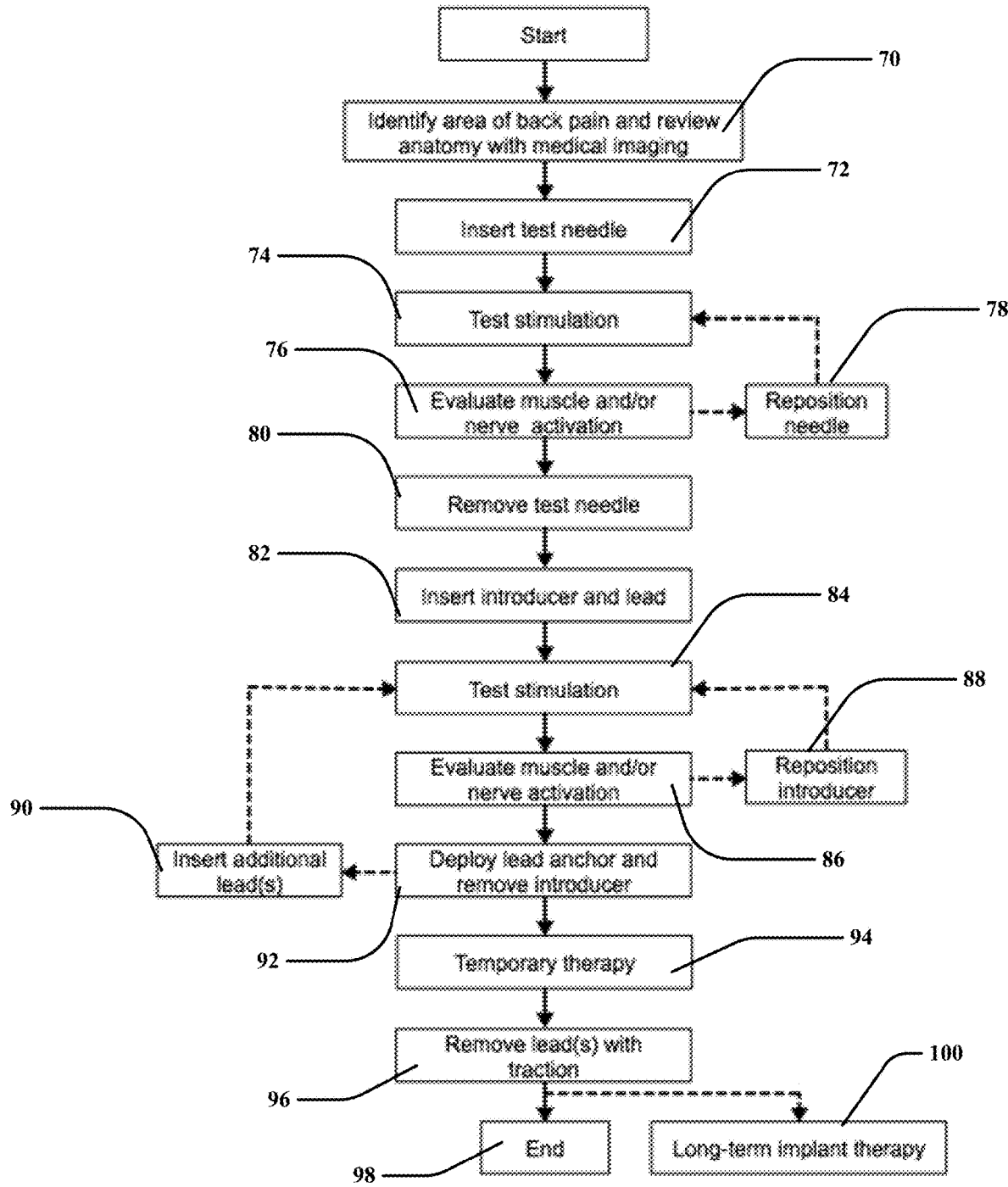
FIG. 11 is a flow diagram of an exemplary method associated with a percutaneous stimulation system in accordance with various embodiments described here.

According to an exemplary method associated with the present stimulation system, in accordance with various embodiments described here, the order of procedures and/or interventions used for lead placement and treatment may be predefined. FIG. 11 depicts an exemplary flowchart of non-limiting method associated with a percutaneous lead system. As a non-limiting example, the clinician may initiate the lead placement procedure by identifying the regions of back pain and/or reviewing anatomy of paraspinal muscles and spine with medical imaging 70, as may be needed to sufficiently plan needle insertion and lead deployment. Insertion of the test needle 72 and test stimulation 74 may be used to activate nerve and produce contractions in paraspinal muscle(s), which may then be used to evaluate the extent 76 and selectivity of nerve activation and may be used to inform the need to reposition needle location 78. The test needle may then be removed 80. In this non-limiting example, following identification of a location that produces desired neural and muscular response to stimulation, the introducer and lead may be inserted in the same trajectory 82 (e.g., insertion location, angle, depth, etc.), testing may be conducted 84, and nerve activation and muscle contractions evaluated 86. The introducer and lead may be repositioned 88 as needed to generate desired activation of selected nerve(s) and paraspinal muscles and/or additional leads 90 inserted to achieve desired total effect of stimulation. Following deployment of the lead(s) 92, the introducer(s) may be removed and the leads connected to the external pulse generator for use at home for a prescribed, temporary period of time (e.g., four weeks) 94. At the end of the temporary therapy, the leads may be easily removed 96 through an appropriate approach (e.g., through gentle traction) and the therapy discontinued 98. In the event of the need for an increase in therapy duration, the patient may undergo implantation with an implanted lead and/or pulse generator to enable sustained pain relief with long-term use of the therapy 100.

Prior to placement of needle(s), electrode(s) and/or lead (s), the most painful regions on each side of a patient's back may be determined through patient-drawn diagrams of pain, verbal description of location of pain, palpation and/or manual evaluation by clinician, and/or other methods. As a non-limiting example, a clinician may use his/her fingers to gently palpate the back, starting within the regions indicated on a pain diagram previously completed by the patient, allowing the patient to indicate the spread of pain and location of greatest pain across the region (e.g., on left and/or right side). The spread (e.g., area, shape) of pain may be marked on the back with a marker and the skin in the area surrounding these regions may be prepared with antiseptic. Topical numbing agent (e.g., lidocaine) may be applied to skin to prevent discomfort from needle insertion. On one or both sides of the back, sterile needle electrode(s) (i.e., test needle) may be inserted below the skin and positioned (e.g., electrode may be located 0.5-1.5 cm away from nerve) to target the dorsal ramus or other nerve (e.g., spinal nerve, distal branches, etc.) and connected to an external pulse generator to deliver electrical stimulation, which may produce activation of the paraspinal muscles (see FIGS. 5, 7A-7J). Anatomical targets and/or needle insertion trajectory may be visualized and/or guided by ultrasound, fluoroscopy, or any other appropriate medical imaging method. Alternatively, the electrode may not be connected to a pulse generator (e.g., the generator may be integrated or pre-connected with the electrode or it may be radio frequency or otherwise wirelessly powered). The electrode(s) may be placed in a lateromedial approach at approximately the same spinal level (e.g., L3, S1) as the most painful area(s), by inserting a fixed distance from the midline (e.g., 2.5 cm) targeting the nerve (e.g., medial branch of the dorsal ramus, see FIGS. 5A-5C, 6A-6C, and 7A-7F). Yet another approach may be to insert the needle at an angle (e.g., another trajectory, such as superoinferior or inferosuperior) at a different site (on the dorsal/posterior, lateral, or ventral/anterior part of the body), so that the tip of the needle may be positioned to target the nerve in or innervating the regions of greatest pain. The depth of the needle insertion and location with respect to anatomical landmarks may be guided by ultrasound, fluoroscopy, medical imaging, or electromyography, or by other known procedures for insertion of needles or the like into the back (e.g., paravertebral injections).

The intensity of the electrical stimulation provided by the pulse generator may be increased and adjusted independently for each lead and/or channel to enable selective stimulation and comfortable activation of muscles with each lead. The extent of muscle activation and/or sensations produced by nerve stimulation may be evaluated with ultrasound to confirm activation in regions of pain, or for example through other applicable methods (e.g., visually by movement of muscle or needle motion, by electromyography, by computer-aided visualization, by changes in electrical conductivity of tissue, patient report of muscle contractions, by manual palpation, by non-human palpation, or by utilizing another imaging modality such as thermal, infrared, or MRI/PET). Confirmation of muscle contractions occurring in the areas of pain (e.g., via patient drawings and/or marked area on back) by ultrasound or any other technique may be used to assess neural activation and may be used to inform repositioning of electrode. Alternatively, muscle contractions may be generated, but may not be able to be observed by the same means. For example, patients may describe experiencing sensations that are associated with muscle contractions, including, but not limited to, tapping, tightening, pinching, cramping, or massaging. Once contractions have been evoked, the location of the needle insertion may be marked, the needle removed, and the positioning of the needle (e.g., depth beneath skin, angle with respect to surface of the skin) may be measured. In other embodiments, stimulation may proceed without confirmation of muscle contractions produced by nerve stimulation. For example, a clinician may use a high intensity likely to cause recruitment of motor nerve fibers and muscle contractions, but the clinician may choose not to verify that muscles have contracted.

The present method may enable the activation of peripheral nerves, including nerve branches and/or individual neural fibers, innervating the entire region of low back pain. The system may produce pain relief through activation of paraspinal muscles across the entire region of back pain sufficient to generate neural signal encoding and modulation of central pain processing in that area. For example, activation of paraspinal muscles may be achieved through direct stimulation of motor nerve fibers, stimulation of motor point of the muscle, and/or activation of motor fibers in the nerve. Targeting the peripheral nerve (e.g., dorsal ramus or spinal nerve branches) may offer an advantage of allowing for widespread activation of paraspinal muscles, as the nerve fans out and sends branches to innervate multiple muscles (e.g., medial-lateral or inferior-superior). Further, this system offers an advantage over technology that stimulates at motor points to provide the local activation of muscles for the purpose of strengthening or stabilizing muscles. The present therapy also provides an advantage over the prior art because stimulation targeting peripheral nerve without need to target motor points may increase the area of activation and reduce need for addition leads or electrodes. This system may produce activation of muscles across the entire region of pain via stimulation of peripheral nerves innervating paraspinal muscles to produce an increase in stimulation-evoked neural-encoded signals and/or afferent activity, which encodes changes in pain processing across the entire region. In an embodiment, targeted activation of the nerve (e.g., trunk and/or branch), which for example, may innervate one or multiple muscles, can produce better activation (e.g., more widespread) of the muscles in the entire area of back pain, critical to produce sufficient neural encoding signals to modulate and/or eliminate central sensitization and restore pain processing. As a non-limiting example, the extent (e.g., intensity, spread, volume, etc.) of activation of the paraspinal musculature (e.g., multifidus, spinal erector, etc.) may be used to indicate the magnitude (e.g., level, spread, activation) of nerve activation (e.g., peripheral and/or spinal nerves, branches or nerve fibers) produced by stimulation.

Figure 8:
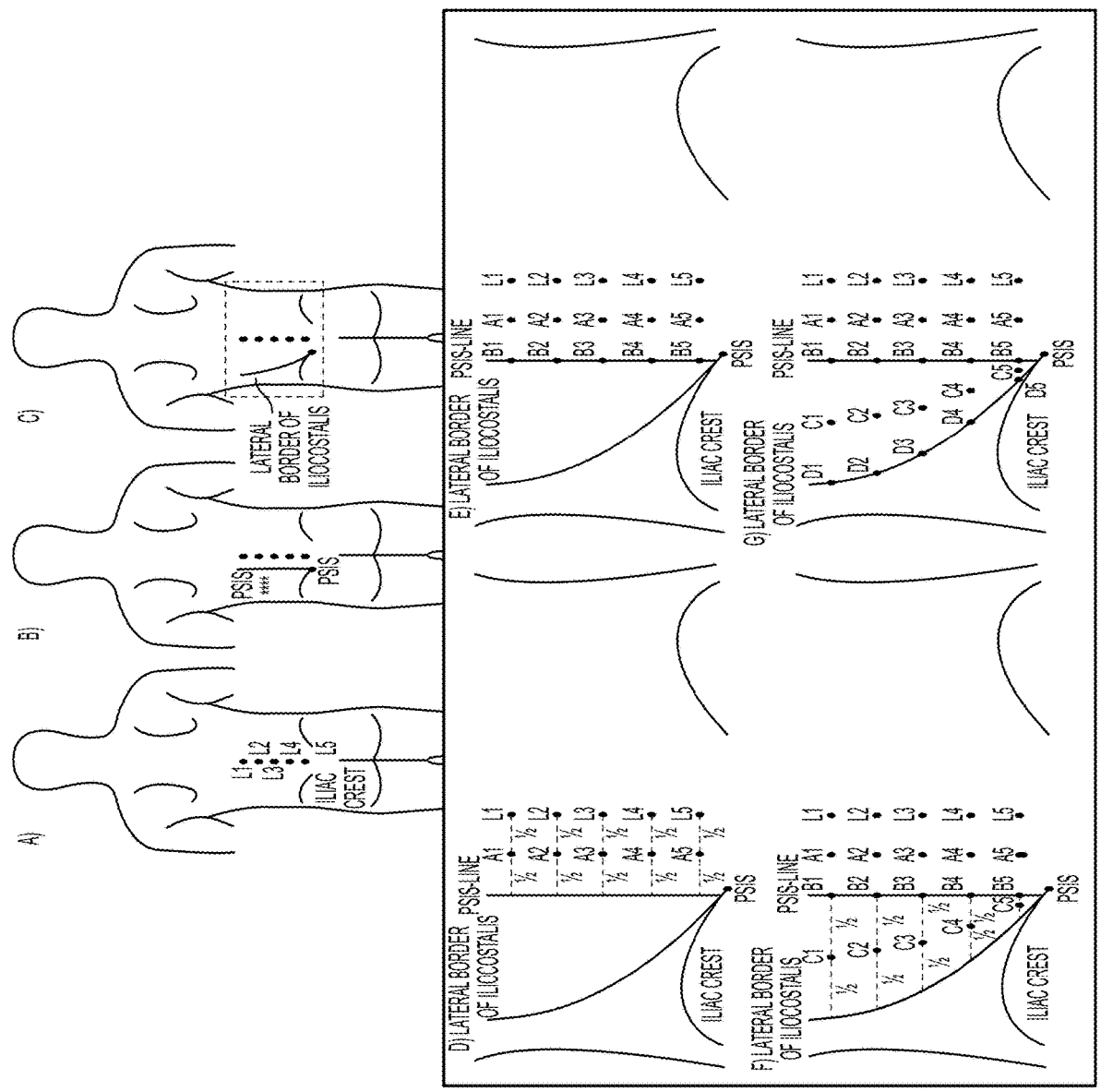
FIG. 8 is an example of a coordinate system to guide electrode placement based on anatomical landmarks including the posterior superior iliac spine (PSIS)

As shown in FIG. 8, percutaneous leads may be placed through entry points on a patient. An introducer may be used at the site or sites identified with the needle electrodes and may be placed at the depth identified previously and using the needle positioning identified previously or the method may be completed without a test needle. Electrode placement may be guided by a predetermined map of nerve and/or muscle response generated by stimulation at different coordinates, where the coordinates may be based on relative or absolute distances from anatomical landmarks. This predetermined map may be individualized for each patient or may be generalized for use across specific groups of patients (e.g., obese patients, tall patients, geriatric patients) or all patients. The patient may be given lidocaine along the anticipated pathway of the percutaneous lead if he or she desires. The leads may be inserted and connected to an external pulse generator of any appropriate configuration. Stimulation may be delivered through the leads to verify proper placement and nerve activation (e.g., as confirmed by stimulation-evoked muscle contractions in the expected location). The introducers may be removed, leaving the leads within the target tissues.

Following placement, the proximal portion of the lead, which may reside outside of the patient's body, may be secured to the skin and covered with a waterproof bandage. Prior to leaving the clinic, a patient may be instructed on the proper care of the lead exit sites. Patients may be inspected afterwards (e.g., within 48 hours) for analysis of the leads and exit sites. The leads may be allowed to stabilize for a period of time (e.g., one day to one week) before the treatment period begins, or the treatment therapy may begin immediately after the completion of lead placement. FIG. 11 depicts an exemplary flowchart of non-limiting method associated with a percutaneous lead system, according to various aspects of the subject disclosure.

Leads with stimulating electrodes may be placed (e.g., in any tissue, at any distance from the nerve and/or muscle) to target the dorsal (posterior) ramus and/or branches of the spinal nerves to yield activation of paraspinal muscle(s) and this approach may be generalized to produce activation and/or sensation in any nerve branch and/or muscle in the back, including, but not limited to, multifidus, erector spinae, longissimus, iliocostalis, spinalis, latissimus dorsi, rhomboid, serratus posterior, oblique external, oblique internal, quadratus lumborum, psoas major, psoas minor, trapezius, levator scapulae, splenius capitis, splenius cervicis, semispinalis muscles, rotatores muscles, rectus capitis posterior muscles, interspinales, levatores costarum, obliquus capitis inferior muscle, obliquus capitis superior, rectus capitus posterior major, and rectus capitus posterior minor.

Figure 9A:
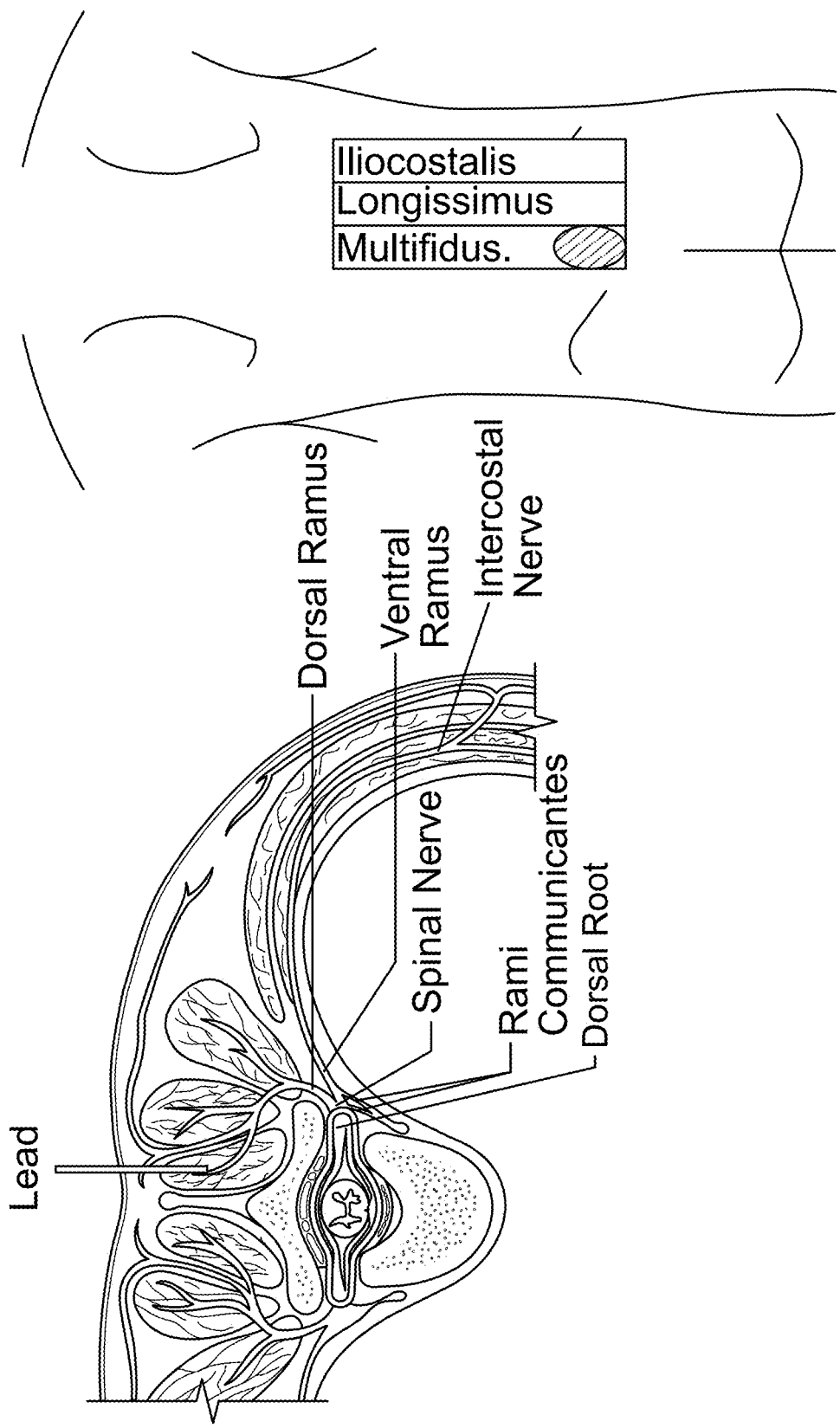
FIGS. 9A-9J illustrate placement of the percutaneous lead(s) into the muscles of the back and the associated regions of muscle activation.
Figure 9B:
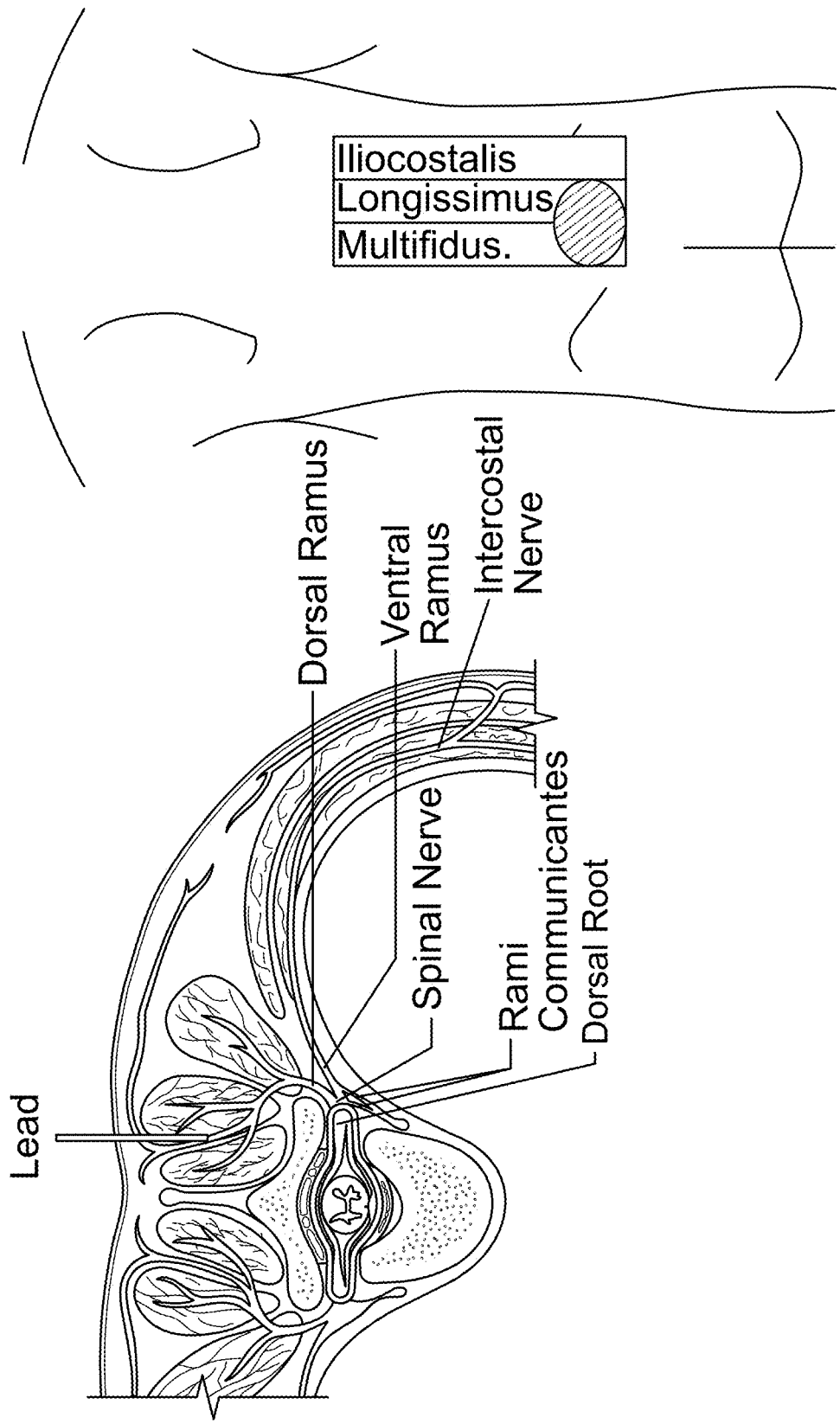
Figure 9C:
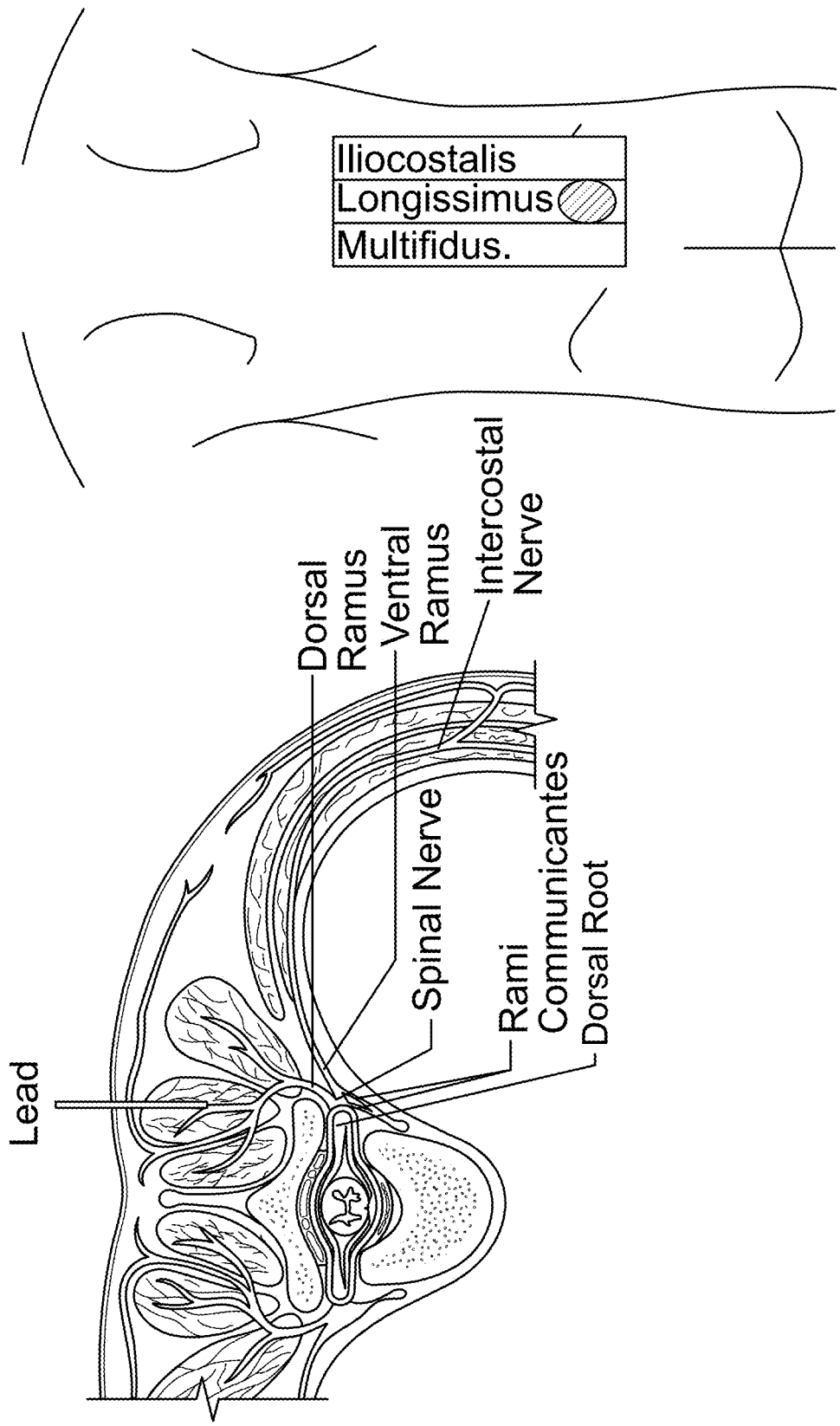
Figure 9D:
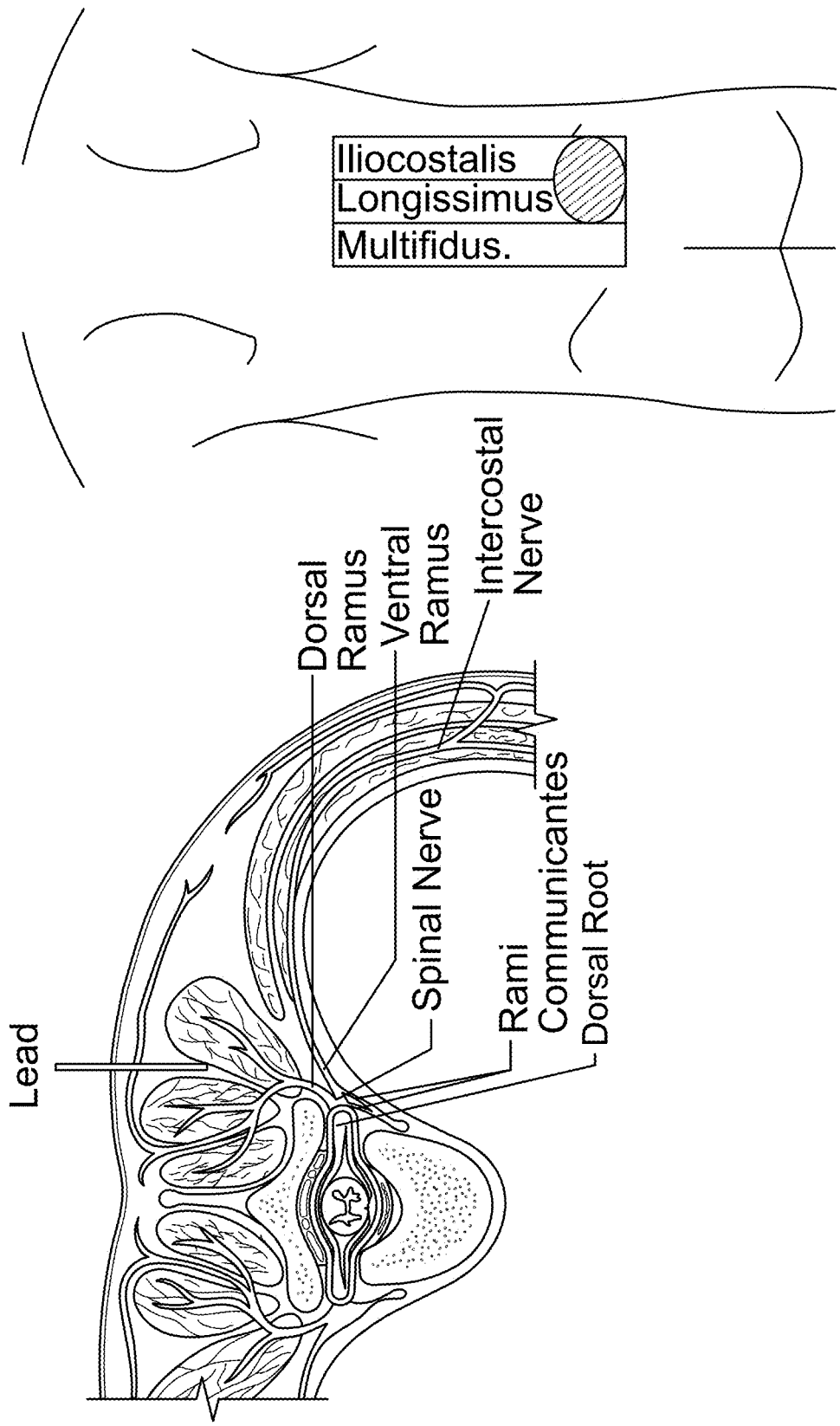
Figure 9E:
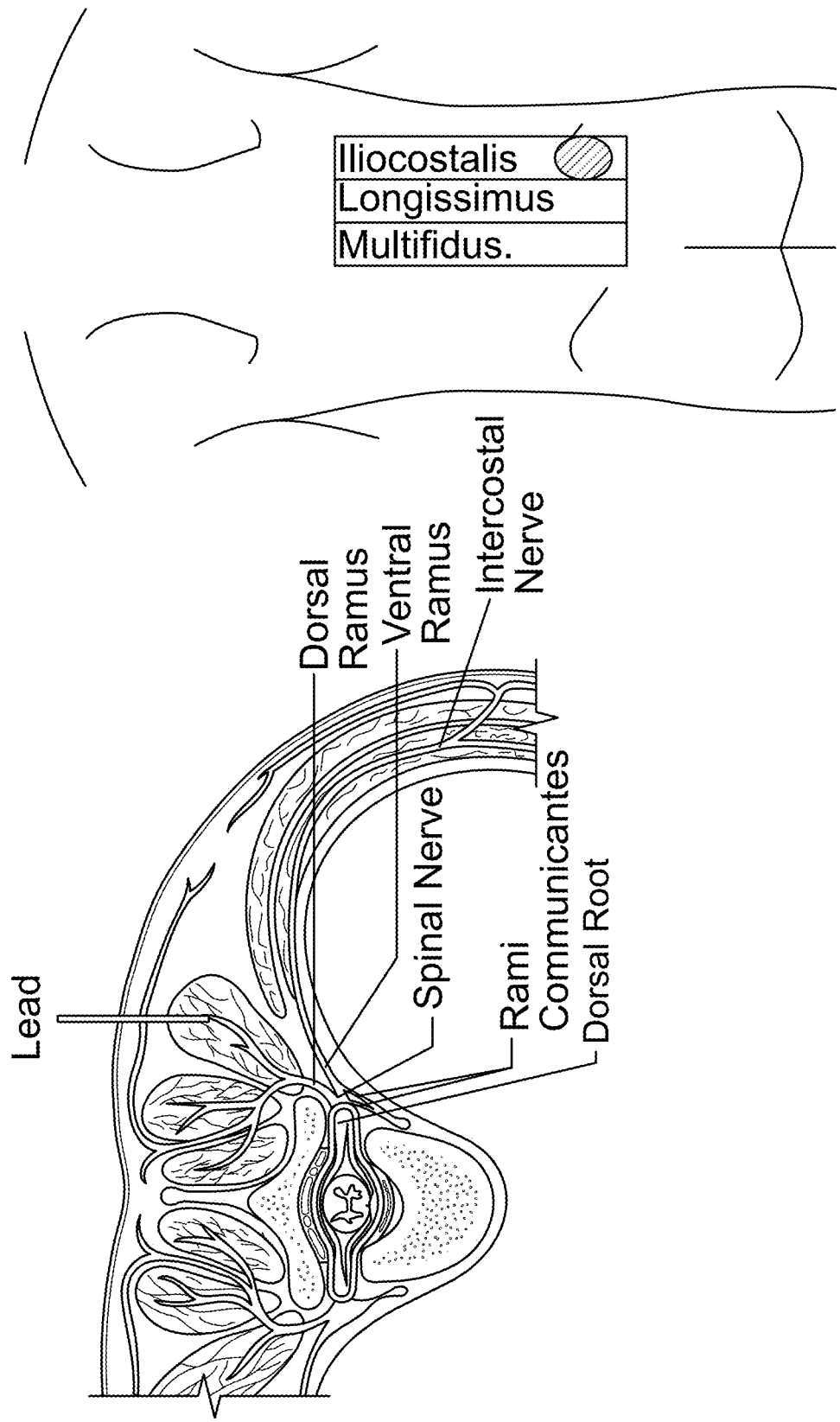
Figure 9F:
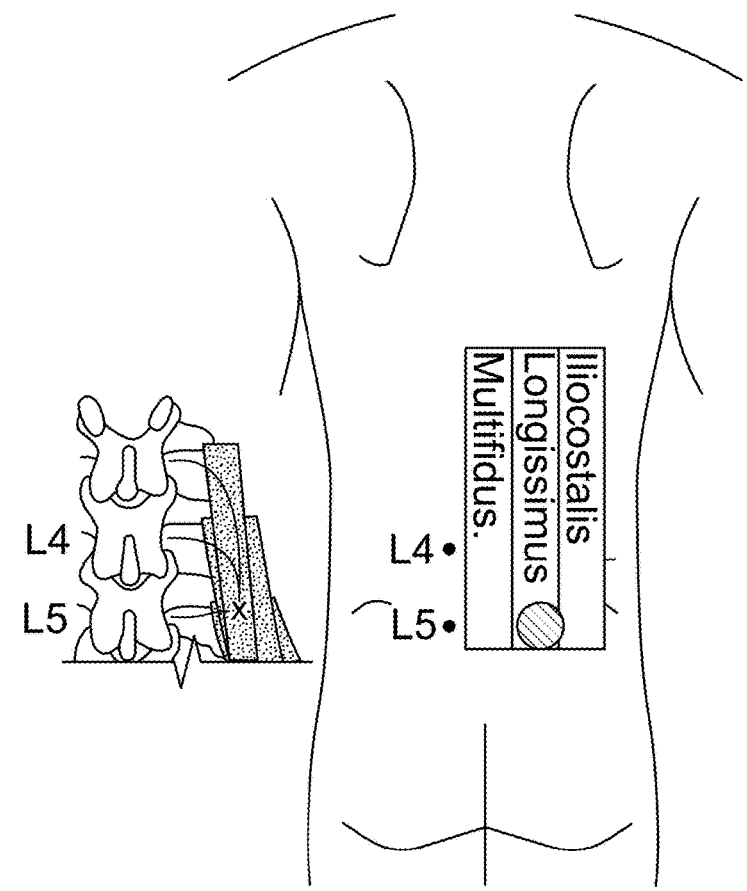
Figure 9G:
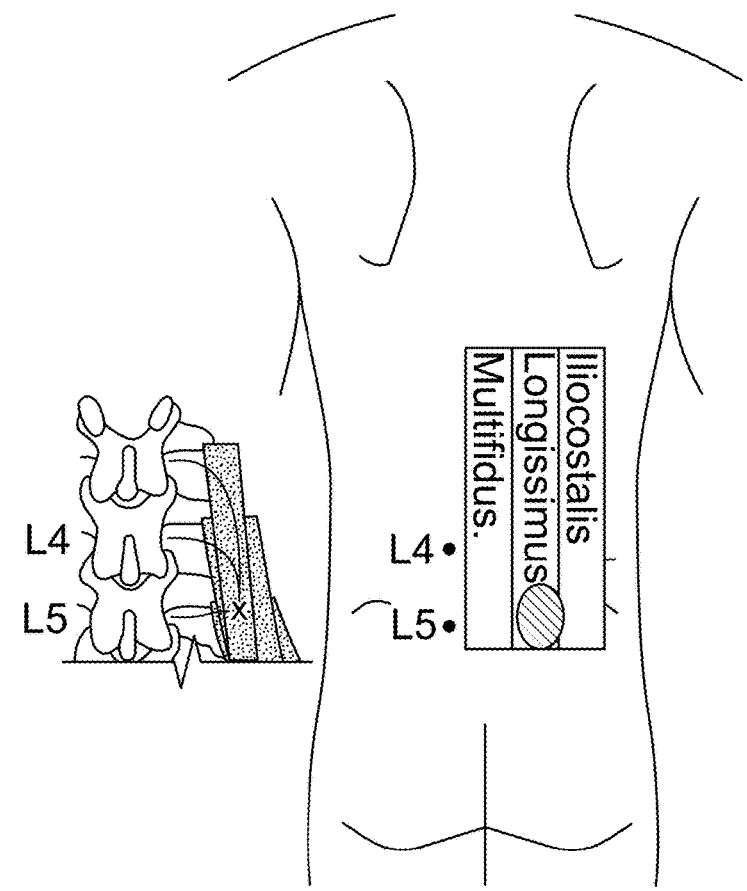
Figure 9H:
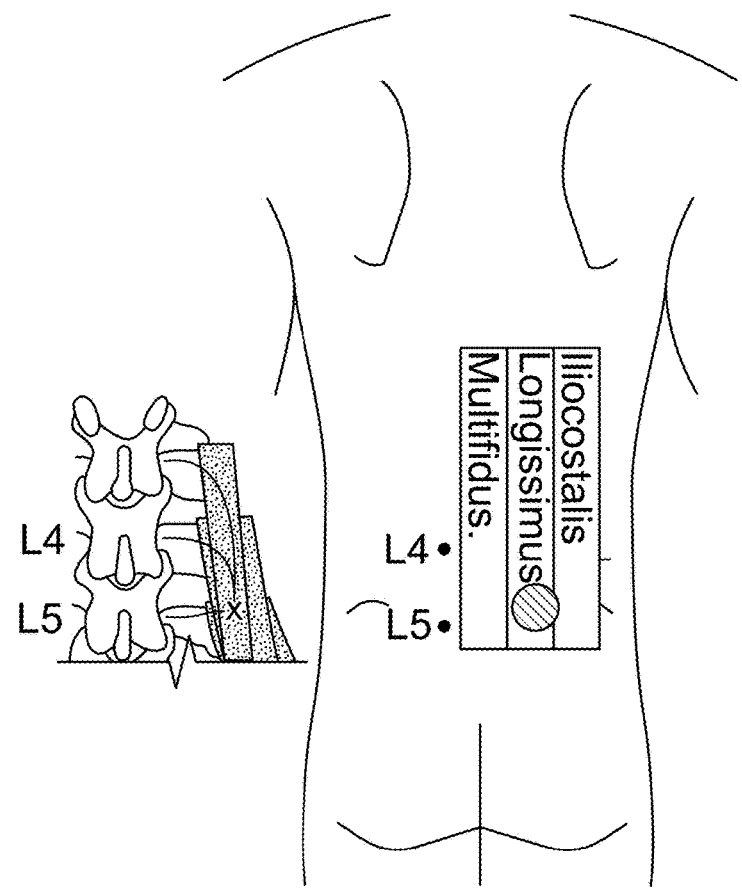
Figure 9I:
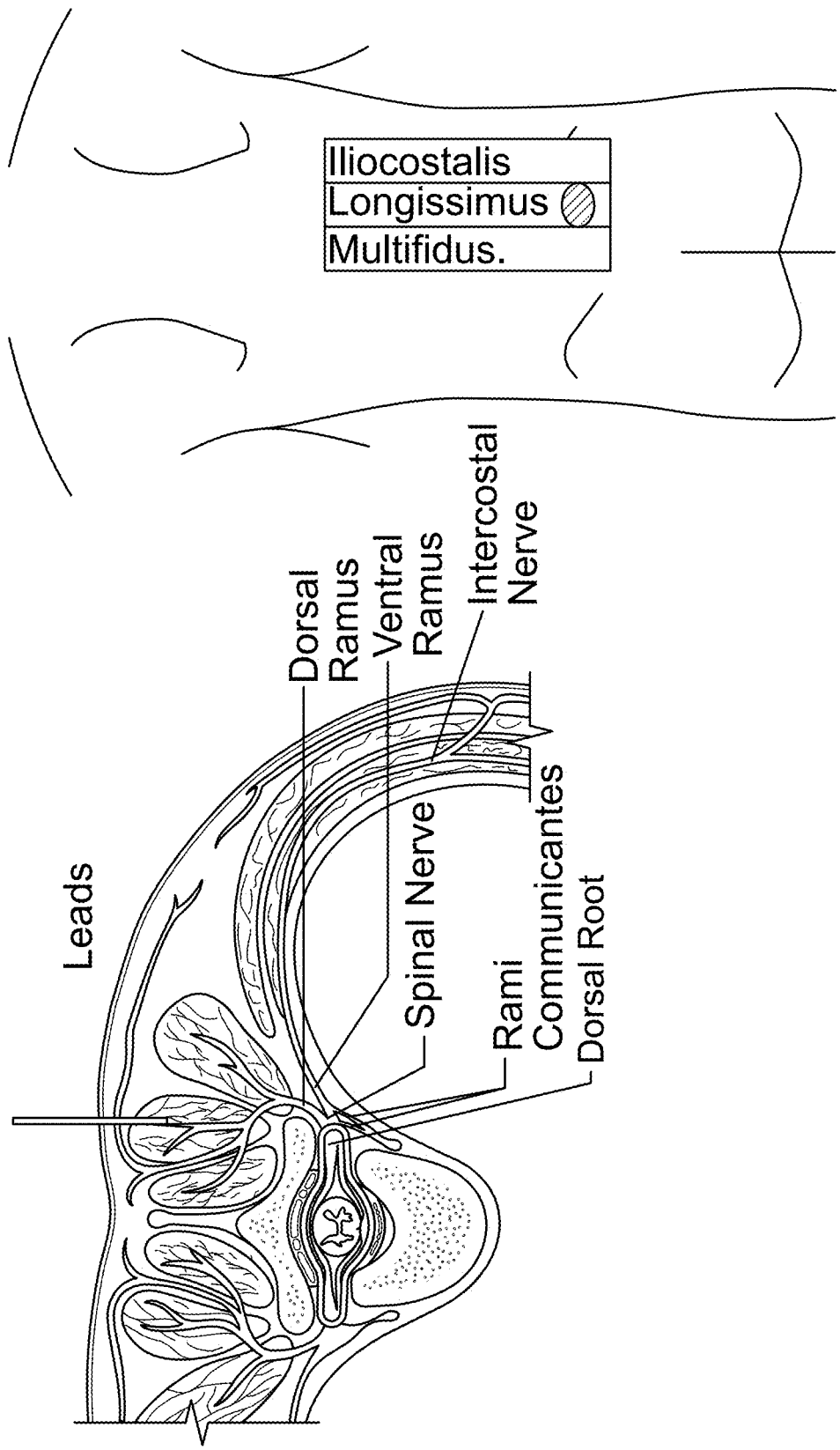
Figure 9J:
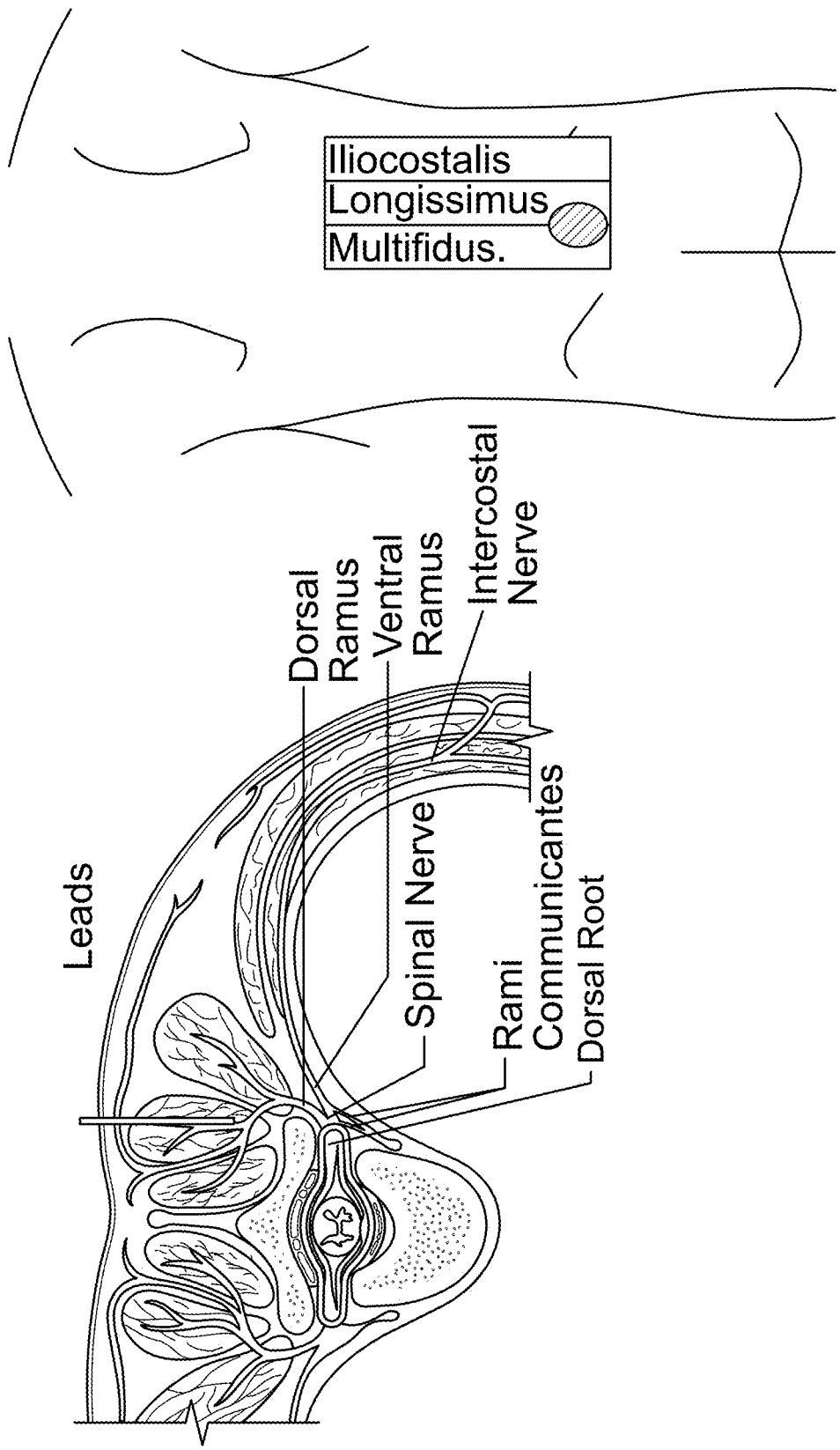
Figure 10:
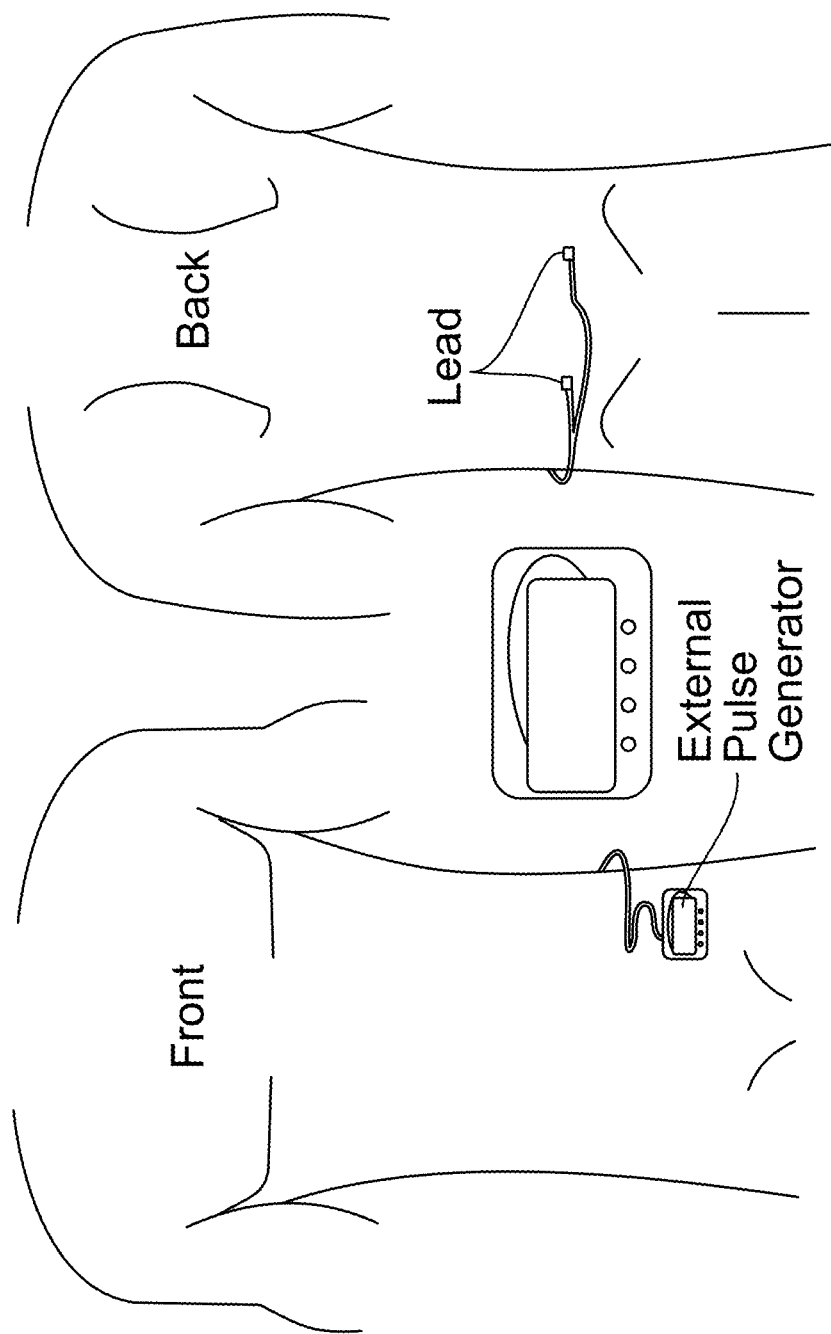
FIG. 10 illustrates placement of the percutaneous leads and pulse generators on a patient's body.

The lead may need to be repositioned to generate comfortable muscle contractions in a different part of the back, and this may be achieved based on known innervation patterns for the paraspinal muscles or any other appropriate muscle or muscle group. For example, because the medial, intermediate, and lateral branches of the dorsal ramus innervate lumbar paraspinal muscles positioned in the same medial-lateral order (i.e., multifidus, longissimus, iliocostalis) (FIG. 4), the lead may be repositioned medially or laterally to generate more medial or lateral muscle activation, respectively (FIGS. 9A-E). Similarly, because the paraspinal muscles are generally segmentally innervated, the lead may be repositioned more superior or inferior to generate more superior or inferior muscle activation, respectively (FIGS. 9F-H). The depth of the lead may also generate different regions of muscle activation due to the branching patterns of the dorsal ramus and peripheral nerves (FIGS. 9C, 9I, and 9J).

Use of systems and methods according to the present teachings may be expected to generate comfortable targeted activation of back muscles anywhere there is pain, including, without limitation the lumbar, thoracic, cervical, and sacral levels. Percutaneous electrical stimulation may be expected to generate comfortable targeted activation of muscles that overlap the region of greatest pain. The stimulation of nerves and subsequent activation of back muscles may also be generated that are near, but outside of the region of pain. The location of the target back muscles may be unrelated to the region of pain and may be selected based on other criteria (e.g., patient age, weight, height, medical history) or may be the same for all patients. The pain may be acute, subacute, or chronic back pain. If the stimulation is used to treat acute or subacute pain, it may be used to prevent chronic pain in the future.

In an embodiment, the lead may be positioned in a specific location in a muscle (e.g., in body of paraspinal muscle) to produce activation of a nearby neural target (e.g., dorsal ramus, spinal nerve, peripheral nerve). This type of indirect activation of the dorsal ramus may provide an ability to vary various factors of the lead and the pulses that it delivers to generate the desired response. For example, with indirect activation of nerves (e.g., motor nerves innervating paraspinal muscles), the amplitude, pulse duration, and/or frequency of the pulses may be varied.

The present system may enable selective targeting of the large motor fibers of peripheral and/or spinal nerves (e.g., medial, intermediate, lateral branches of the posterior (dorsal) ramus lumbar spinal nerve). Comfortable activation of muscles (e.g., as is required for a therapy that may be well tolerated by patients) may be produced by selective activation of nerve fibers (e.g., motor fiber(s) innervating muscle fiber(s)) that avoids activation of unwanted fibers (e.g., pain-generating cutaneous fibers). The branches of the dorsal rami and other peripheral nerves innervating the paraspinal muscles contain not only motor axons, but also sensory axons. The present system and methodology may enable selective stimulation to activate motor fibers (e.g., without activation of sensory fibers) and provide means for selective control of muscles (e.g., paraspinal muscles in regions of back pain). This approach, using one or more leads placed in tissue to target nerves to generate muscle contractions, may avoid cutaneous discomfort since stimulation is delivered away from cutaneous receptors and closer to target peripheral motor neurons. While activation of motor axons causes muscle activation, it may not be expected to cause discomfort.

Motor axons typically have a larger diameter than the sensory axons that transmit the signals that lead to the perception of pain. The strength (i.e., intensity) of electrical stimulation required to activate axons increases as axon diameter decreases. Thus, motor axons should be activated at lower stimulation intensities than sensory axons, enabling comfortable activation of motor axons without activation of painful sensory axons. Further, because of the placement of the leads subcutaneously within tissue, electrical stimulation may be delivered far from cutaneous receptors and may avoid the painful sensations generated during other methods, such as TENS.

Stimulation that activates large diameter motor fibers while avoiding stimulation of small diameter sensory fibers enables selective control of paraspinal muscles and avoids unwanted side effects of stimulation, such as discomfort or pain caused by stimulation. Methods to enable selective stimulation include electrode design and shape, location of electrode deployment, pattern of stimulation. In one embodiment, the present system employs a percutaneous, monopolar lead with self-anchoring tip electrode that permits activation of peripheral nerves from a greater distance than other electrode and/or lead designs (e.g., bipolar, cylindrical contacts). In a non-limiting example, the present system facilitates fast, simple, minimally-invasive deployment of the stimulating lead to produce this selective neural fiber stimulation via a targeted peripheral nerve stimulation approach, which minimizes the procedural risks and discomfort for the patient. Therefore, the present system presents an advantage over the prior art of invasive and complex surgical procedures (e.g., to place electrodes or leads in spinal cord stimulation or other implanted peripheral nerve or neuromuscular stimulation modalities), as this system enables fast, minimally-invasive, and reliable lead placement to target spinal and/or peripheral nerves and produce activation of muscles to modulate central pain processing.

Traditionally there are multiple potential sources of iatrogenic pain during the delivery of electrical stimulation for the treatment of back pain, but because the system invention is targeting the modulation of pain processing by stimulating efferent nerve fibers to generate comfortable (e.g., but non-functional) muscle contractions with a unique method of stimulation that evokes neural activity in afferent fibers capable of modulating central pain processing and decreasing the perception of pain, the present system can avoid causing discomfort or pain during and after the delivery of stimulation.

Parameters (e.g., frequency and amplitude) of the stimulation applied may be variable, but in some embodiments may be fixed. Intensity may be modulated by varying the amplitude and/or pulse duration. Stimulation intensity may be set to generate comfortable muscle contractions that may be mild, moderate, or strong. As shown in FIG. 9, each of the two percutaneous leads or connecting cables may be wrapped around a patient's respective side and connected to a pulse generator, such as a body-worn external pulse generators located on the front or side of the abdomen. In other embodiments, the external pulse generator may be placed on any appropriate location, including, without limitation on the back, legs, or arms. Over the treatment period (e.g., four weeks or within an approximate range of 1-12 weeks), a patient may self-administer stimulation every day for a daily treatment time (e.g., 6-12 hours per day, less than or up to 24 hours per day) through a single or multiple sessions (e.g., 6 hours of stimulation may be divided up into two 3-hour sessions, or one 6-hour session). Patients may be able to partake in their normal routines during stimulation. A patient may use the system in any bodily position (e.g., while sitting, standing or laying down (supine, prone, or laying down on one's side)). The stimulator may maintain an electronic log for compliance monitoring. In other embodiments, stimulation may be administered under the guidance of a clinician (e.g., in an office, or clinic). At the end of the treatment period, the leads may be removed in any appropriate manner, such as by applying gentle traction.

The system may enable pain relief via comfortable stimulation and/or activation of nerves and/or muscles without producing discomfort. The system may enable this comfortable pain relief by enabling selective neural activation and avoiding activation of undesired neural (e.g., cutaneous nociceptive fibers or pain fibers) and/or motor fibers. Furthermore, the present system may enable comfortable administration of stimulation therapy by circumventing motor fatigue and/or discomfort resulting from activation of nerves and/or musculature produced by other therapies (e.g., tonic and/or intermittent contractions which are produce muscle fatigue). As a non-limiting example, the system may enable stimulation with parameters (e.g., duty cycle, frequency, pulse duration, ramp time, etc.) that, when applied to peripheral nerve and/or muscles, facilitate patient comfort. Further, the selection of stimulation parameters may be tuned to avoid fatigue muscles and enable selective, comfortable activation of peripheral nerves and/or muscles. In an embodiment, pain relief with the present therapy may be achieved through short-term, periodic sessions (e.g., 6-12 hours per day or less than or up to 24 hours per day) without requiring continuous stimulation (e.g., tonic or persistent). In another non-limiting example, stimulation may be applied at specific frequencies (e.g., low frequencies, 5-20 Hz) that produce consistent motor activation and the generation of afferent signals to modulate pain processing, without producing fatigue (e.g., which could prevent encoding of neural signals and generation of pain relief). Furthermore, the stimulation parameters may administer stimulation and activation of muscle fibers that is comfortable and may enable patients to continue activities of daily living, presenting an advantage over existing therapies and the prior art where stimulation must be applied over prolonged periods of time (e.g., continuous) and/or stimulation and/or sensations for stimulation may be distressing (e.g., stimulation intensity causes additional pain and/or prevents patients from engaging in activities of daily living). Furthermore, the system may enable pain relief through activation of nerves that is well tolerated by patients and avoids the need for down-time (e.g., recovery, delay, etc.) following the procedure, providing the advantage that the therapy can begin immediately and improving likelihood of patient benefit and/or pain relief.

The present system may modulate central neural processing (e.g., in the CNS, such as the spinal cord, brain, and/or other central neural processing centers) to reduce the perception of pain, and this modulation of central neural processing is achieved without requiring blocking of transmission of pain signals from periphery (e.g., through peripheral and/or spinal nerves and distal branches) to the central nervous system. As a non-limiting example, the proposed therapy may make use of existing natural processes of neural signal encoding by muscles, evoked through nerve stimulation, which can modulate pain processing, without use of and avoiding signal transmission blockade (e.g., neuroablative procedures or surgery, which permanently damage nerves and seek to block transmission of signals to central processing centers). The system may directly addresses the manifestation of pain at the central neural processing level, unlike other systems, which focus on modifying or blocking incoming signals from the periphery (i.e., failing to address cause of pain).

The present system may modulate central neural processing (e.g., in the CNS, such as the spinal cord, brain, and/or other central neural processing centers) to reduce the perception of pain, and this modulation of central neural processing is achieved without requiring blocking of transmission of neural (e.g., nerve or nerve fiber) signals from periphery (e.g., through peripheral and/or spinal nerves and distal branches) to and/or from the central nervous system. The present system may modulate central neural processing without nerve blocking because the invention enables reduction and/or elimination of pain via modulation of central neural processing (i.e., nerve block is not required and the present invention desirably avoids nerve block). The present invention provides back pain relief without nerve block and the present invention provides back pain relief while avoiding nerve block.

During the treatment period (e.g., three weeks) the treatment may reduce pain while stimulation is on, and may lead to reduced pain while stimulation is off. The nerve stimulation and resulting muscle contractions may provide pain relief that may also persist after the treatment period (carryover effect) for several minutes to several months. Thus, this temporary (e.g., four weeks) treatment may provide long-term pain relief at least as long as the treatment period itself (e.g., three weeks to one year). Further, this treatment may cause change to the nervous system that relieves pain.

Compared to individuals with healthy backs, patients with chronic back pain have reduced function, health-related quality of life, and range of motion. When treatments reduce chronic back pain, function, health-related quality of life, and range of motion improve. As a result, the reductions in chronic back pain generated by the system may be expected to result in improvements in function and significant improvements in health-related quality of life and range of motion. When combined with other back pain therapies, may enhance overall effectiveness.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

The invention claimed is:

1. A method to alleviate back pain, the method comprising the steps of:
placing a monopolar electrode within a tissue of an animal body, and applying electrical stimulation through the monopolar electrode through an external electrical stimulator to activate: (i) at least one efferent nerve fiber of the dorsal ramus of the animal body relieving pain and (ii) at least one paraspinal muscle without strengthening the paraspinal muscle.

2. The method of claim 1, further comprising the step of modulating central neural processing through the activation of the at least one nerve near the dorsal ramus of the animal body.

3. The method of claim 2, further comprising the step of producing an increase in stimulation-evoked neural encoded signals.

4. The method of claim 3, further comprising the step of producing a change in efferent nerve fiber activity.

5. The method of claim 4, further comprising the steps of evaluating an area of back pain.

6. The method of claim 5, further comprising the step of repositioning the monopolar electrode at a location based on the area of back pain.

7. The method of claim 6, further comprising the step of applying electrical stimulation through the monopolar electrode that has been repositioned.

8. The method of claim 7, wherein the alleviation of back pain persists after the stimulation is discontinued.

9. The method of claim 8, further comprising the steps of: inserting an additional electrode; applying electrical stimulation through the additional electrode; and comparing an area of muscle activation caused by the electrical stimulation with an area of pain.

10. The method of claim 9, further comprising the steps of: removing the monopolar electrode; applying an electrical stimulation through the additional electrode; and re-comparing a second area of muscle activation caused by the electrical stimulation with the area of pain.

11. An electrical stimulation device comprising:
a monopolar electrode adapted for insertion within an animal body with back pain;
a percutaneous lead operatively coupled with the monopolar electrode; and
at least one pulse generator external to the animal body and operatively coupled with the electrode through the percutaneous lead, wherein the pulse generator delivers electrical stimulation activating at least one efferent nerve fiber of the dorsal ramus of the animal body for pain relief thereby resulting in activation of at least one paraspinal muscle without strengthening the paraspinal muscle.

12. The electrical stimulation device of claim 11, wherein the percutaneous lead a coiled lead.

13. The electrical stimulation device of claim 12, wherein the percutaneous lead includes an insulated portion and a deinsulated portion whereby the deinsulated portion forms the monopolar electrode.

14. The electrical stimulation device of claim 13, wherein the percutaneous lead is implanted in the paraspinal muscle.

15. The electrical stimulation device of claim 13, wherein the percutaneous lead includes a barb formed from the deinsulated portion.

16. The electrical stimulation device of claim 13, wherein the percutaneous lead includes a taper between the insulated portion and deinsulated portion.

17. The electrical stimulation device of claim 1, wherein the pulse generator delivers electrical stimulation activating the efferent nerve fiber in the back for a treatment period.

18. A method to alleviate back pain, the method comprising the steps of:
utilizing an electrical stimulation device in an animal body, the electrical stimulation device comprising:
at least one electrode adapted for insertion below skin of an animal body with back pain; and
an external pulse generator operatively coupled with the at least one electrode, wherein the external pulse generator delivers electrical stimulation for a prescribed period of time to activate an efferent nerve fiber of the dorsal ramus in a back of the animal body to cause muscle contraction to relieve pain without strengthening a paraspinal muscle activated by the efferent nerve fiber, said relief of pain lasting longer than the prescribed period of time.

19. The method of claim 18, wherein the prescribed period of time is up to 24 hours per day for approximately one to twelve weeks.

20. The method of claim 19, wherein the electrical stimulation device further comprises at least one lead.

21. The method of claim 20, wherein the at least one lead is percutaneous.

22. The method of claim 20, wherein the at least one lead is implanted in the tissue of the animal body.

23. The method of claim 22, wherein the tissue is a paraspinal muscle.

24. The method of claim 22, wherein the electrical stimulation device provides long-term use of greater than three weeks.

* * * * *